US 12,091,502 B2

United States Patent
Yoshimura et al.

(10) Patent No.: US 12,091,502 B2
(45) Date of Patent: Sep. 17, 2024

(54) HETEROBIFUNCTIONAL COMPOUND HAVING MONODISPERSED POLYETHYLENE GLYCOL IN MAIN CHAIN AND SIDE CHAIN

(71) Applicant: NOF CORPORATION, Tokyo (JP)

(72) Inventors: Kohei Yoshimura, Kawasaki (JP); Takuma Tsubusaki, Kawasaki (JP); Mika Hamura, Kawasaki (JP); Yuki Matsuno, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 1045 days.

(21) Appl. No.: 16/978,918

(22) PCT Filed: Mar. 11, 2019

(86) PCT No.: PCT/JP2019/009779
§ 371 (c)(1),
(2) Date: Sep. 8, 2020

(87) PCT Pub. No.: WO2019/176875
PCT Pub. Date: Sep. 19, 2019

(65) Prior Publication Data
US 2021/0047465 A1 Feb. 18, 2021

(30) Foreign Application Priority Data
Mar. 13, 2018 (JP) .................. 2018-044992

(51) Int. Cl.
| | |
|---|---|
| C08G 65/332 | (2006.01) |
| A61K 47/68 | (2017.01) |
| C08G 65/333 | (2006.01) |
| C08G 65/334 | (2006.01) |

(52) U.S. Cl.
CPC .......... *C08G 65/3322* (2013.01); *A61K 47/68* (2017.08); *C08G 65/33317* (2013.01); *C08G 65/334* (2013.01)

(58) Field of Classification Search
CPC .......... C08G 65/3322; C08G 65/33317; C08G 65/334; A61K 47/68
See application file for complete search history.

(56) References Cited

U.S. PATENT DOCUMENTS

| | | |
|---|---|---|
| 2003/0065134 A1 | 4/2003 | Sakanoue et al. |
| 2011/0245509 A1 | 10/2011 | Nakamoto et al. |
| 2012/0282671 A1 | 11/2012 | Zhao et al. |
| 2013/0022669 A1 | 1/2013 | Axelsson et al. |
| 2013/0172576 A1 | 7/2013 | Kamiya et al. |
| 2013/0225789 A1 | 8/2013 | Sun et al. |
| 2014/0135486 A1 | 5/2014 | Zhao et al. |
| 2015/0165071 A1 | 6/2015 | Takahashi et al. |
| 2019/0117790 A1 | 4/2019 | Song et al. |
| 2020/0000933 A1 | 1/2020 | Tsubusaki et al. |

FOREIGN PATENT DOCUMENTS

| | | |
|---|---|---|
| CN | 104744685 A | 7/2015 |
| JP | 2003-113241 A | 4/2003 |
| JP | 2009-503201 A | 1/2009 |
| JP | 2011-225860 A | 11/2011 |
| JP | 2013-75975 A | 4/2013 |
| JP | 2013-515791 A | 5/2013 |
| JP | 2013-523943 A | 6/2013 |
| JP | 2014-185138 A | 10/2014 |
| WO | 02/060978 A1 | 8/2002 |
| WO | 2007/016560 A2 | 2/2007 |
| WO | 2015/057699 A2 | 4/2015 |
| WO | 2016/063006 A1 | 4/2016 |
| WO | 2017/210963 A1 | 12/2017 |
| WO | 2018/181059 A1 | 10/2018 |

OTHER PUBLICATIONS

Lyon, Robert P. et al., "Reducing hydrophobicity of homogeneous antibody-drug conjugates improves pharmacokinetics and therapeutic index", Nature Biotechnology, Jul. 2015, vol. 33, No. 7, pp. 733-736.
International Search Report (PCT/ISA/210) issued May 21, 2019 by the International Searching Authority in counterpart International Patent Application No. PCT/JP2019/009779.
Written Opinion (PCT/ISA/237) issued May 21, 2019 by the International Searching Authority in counterpart International Patent Application No. PCT/JP2019/009779.
Communication dated Jul. 16, 2021 issued by the Intellectual Property India Patent Office in application No. 202047039058.
Zacchigna, M., et al., "Multimeric, Multifunctional Derivatives of Poly(ethylene glycol)", Polymers, 2011, vol. 3, pp. 1076-1090.
Office Action issued Jul. 26, 2022 by the Japanese Patent Office in counterpart Japanese Patent Application No. 2019-043406.

*Primary Examiner* — Samantha L Shterengarts
*Assistant Examiner* — Jed A Kucharczk
(74) *Attorney, Agent, or Firm* — Sughrue Mion, PLLC

(57) ABSTRACT

A heterobifunctional monodispersed polyethylene glycol represented by the formula (1):

$$R^1-(OCH_2CH_2)_n-O-CH_2 \diagdown \atop C \diagup A^1-(OCH_2CH_2)_l-C^1-X^1$$
$$R^1-(OCH_2CH_2)_n-O-CH_2 \diagup \qquad B^1-Y^1$$

(1)

wherein $X^1$ and $Y^1$ are each an atomic group containing a functional group capable of forming a covalent bond upon a reaction with a functional group present in a biofunctional molecule, the functional group contained in the atomic group $X^1$ and the functional group contained in the atomic group $Y^1$ are different from each other; $R^1$ is a hydrocarbon group having from 1 to 7 carbon atoms or a hydrogen atom; n is an integer of 3 to 72; l is an integer of 2 to 72; and $A^1$, $B^1$ and $C^1$ are as defined herein.

12 Claims, 3 Drawing Sheets

HETEROBIFUNCTIONAL COMPOUND HAVING MONODISPERSED POLYETHYLENE GLYCOL IN MAIN CHAIN AND SIDE CHAIN

CROSS-REFERENCE TO RELATED APPLICATIONS

This application is a National Phase Entry of PCT International Application No. PCT/JP2019/009779 filed Mar. 11, 2019, which claims priority to Japanese Patent Application No. 2018-044992 filed Mar. 13, 2018.

TECHNICAL FIELD

The present invention relates to a heterobifunctional compound having monodispersed polyethylene glycol in a main chain and a side chain and having two different chemically reactive functional groups. More particularly, it relates to a heterobifunctional compound having monodispersed polyethylene glycol in a main chain and a side chain and having two different chemically reactive functional groups, which is used for modification of a biofunctional molecule such as a physiologically active protein, a peptide, an antibody, a nucleic acid or a low-molecular weight drug, a drug carrier in a drug delivery system, a diagnostic material, a medical device or the like and which is particularly useful for modification of an antibody drug.

BACKGROUND ART

An antibody-drug conjugate (Antibody-Drug Conjugate: ADC) is an antibody drug in which a drug is bonded to an antibody and which aims to actively carry the drug to a disease site by utilizing the antigen specificity of the antibody. In recent years, it is one of the most rapidly growing techniques in the field of cancer treatment. ADC is composed of each part of an antibody, a drug and a linker for linking the antibody and the drug.

Many of the drugs used in ADC are hydrophobic and when a plurality of these hydrophilic drugs are bonded to an antibody to prepare ADC, there is a problem of occurrence of aggregation or decrease in stability of the antibody in blood, which are caused by the hydrophobicity of the drugs. Accordingly, the number of the drugs which can be mounted per antibody is restricted and as a result, the medical effect of ADC cannot be sufficiently obtained in some cases.

One of the solutions to be investigated for the problem is the use of a hydrophilic linker. As the hydrophilic linker, polyethylene glycol, a hydrophilic peptide, a sugar chain and the like are used. In particular, since polyethylene glycol has a low antigenicity and a high biocompatibility, it is used in a plurality of ADC in clinical trial and preclinical trial stages.

In the field of ADC, for the purpose of guaranteeing the uniformity of ADC and simplifying purification, analysis and drug approval application thereof, a compound containing 90% or more of a component having a specific ethylene glycol chain length is used. Such a compound is referred to as monodispersed polyethylene glycol.

In the case where the monodispersed polyethylene glycol is used as a linker for ADC, since it is necessary to separately bond an antibody and a drug, a heterobifunctional monodispersed polyethylene glycol having two different chemically reactive functional groups is utilized. In general, ADC is prepared using a compound having chemically reactive functional groups different from each other at both terminals of a monodispersed polyethylene glycol chain.

However, in recent years, there has been reported ADC in which monodispersed polyethylene glycol is not used as a linker main chain that links an antibody and a drug and monodispersed polyethylene glycol is introduced as a side chain into a branched linker that links an antibody and a drug.

In Non Patent Literature 1, the pharmacokinetics and therapeutic effect are compared between ADC in which monodispersed polyethylene glycol is used as a linker main chain that links an antibody and a drug and ADC in which monodispersed polyethylene glycol is used as a side chain of a branched linker that links an antibody and a drug, and it is reported that the latter ADC has a high effect of masking the hydrophobicity of the drug and exhibits excellent pharmacokinetics and therapeutic effect.

Further, Patent Literature 2 and Patent Literature 3 disclose various types of ADCs having monodispersed polyethylene glycol as a side chain of a branched linker and intermediates for preparing these ADCs.

Incidentally, Patent Literature 1 discloses a polyethylene glycol derivative having a pentaerythritol backbone and having four polyethylene glycol chains and two types of functional groups at the terminals of the polyethylene glycol chains.

CITATION LIST

Patent Literature

Patent Literature 1: JP-T-2013-515791 (the term "JP-T" as used herein means a published Japanese translation of a PCT patent application)
Patent Literature 2: WO2015/057699
Patent Literature 3: WO2016/063006

Non Patent Literature

Non Patent Literature 1: Nature Biotechnology, 2015, 33, 733-735

SUMMARY OF INVENTION

Problem to be Solved by the Invention

Patent Literature 1 discloses only a compound having four polyethylene glycol chains in a pentaerythritol backbone and two types of functional groups at the terminals of the polyethylene glycol chains. This is because in the reaction of functionalization, the terminal hydroxyl group(s) of a four-chain polyethylene glycol derivative having pentaerythritol as a backbone is derivatized to another functional group(s) and then mono-derivatized or di-derivatized products are obtained by column purification.

In the case where ADC is prepared using the polyethylene glycol derivative disclosed in Patent Literature 1, ADC to be prepared is one in which an antibody and a drug are bonded to the terminals of the polyethylene glycol chains, i.e., is ADC in which polyethylene glycol is used as a linker main chain that links the antibody and the drug.

In ADC having monodispersed polyethylene glycol as a side chain of a branched linker as described in Non Patent Literature 1, Patent Literature 2 or Patent Literature 3, there is used an amino acid having an asymmetric carbon in a branched portion of the linker to which the monodispersed polyethylene glycol is bonded.

In the case where a linker having a desired chemical structure is constructed through a various chemical conversion processes using a compound having such a chiral center, a not-desired partial steric inversion or racemization of the chiral center occurs in, for example, acidic or basic reaction conditions, a reaction in the presence of an organic catalyst or inorganic catalyst, or a reaction in the presence of a condensing agent included in the chemical conversion process, and thus there is a possibility of forming a mixture of stereoisomers. It is very difficult to isolate a compound having a desired three-dimensional structure from the mixture of stereoisomers. It is not preferable to link an antibody and a drug using such a mixture of stereoisomers as a linker, because a heterogeneous ADC is formed.

Further, in Patent Literature 2 or Patent Literature 3, ADC having two or more monodispersed polyethylene glycols in the side chain of a branched linker are also disclosed. However, the bonding positions of the respective monodispersed polyethylene glycol side chains are separated and the effect of masking the hydrophobic drug due to the "umbrella-like structure" (Biomaterials 2001, 22(5), 405-417), which is a characteristic of branched polyethylene glycol having a plurality of polyethylene glycol chains, is small, so that the advantage due to the presence of a plurality of monodispersed polyethylene glycol side chains cannot be effectively utilized.

An object of the invention is to provide a heterobifunctional monodispersed polyethylene glycol which has monodispersed polyethylene glycol in the main chain, has two adjacent monodispersed polyethylene glycol side chains and does not have a chiral center in the molecular structure, and an antibody-drug conjugate in which an antibody and a drug are bonded by using the same.

Means for Solving the Problem

As a result of the intensive studies to solve the problem described above, the present inventors have developed a heterobifunctional monodispersed polyethylene glycol which is a heterobifunctional compound in which monodispersed polyethylene glycol is present in the main chain and two monodispersed polyethylene glycol side chains are adjacently bonded to each other and which does not have a chiral center in the molecular structure, and an antibody-drug conjugate in which an antibody and a drug are bonded by using the same.

Further, in the heterobifunctional monodispersed polyethylene glycol of the invention, since two monodispersed polyethylene glycol side chains are bonded to a quaternary carbon atom of the branched portion by a stable ether bond, it has a characteristic that it is difficult to be decomposed into a single-chain monodispersed polyethylene glycol in the chemical conversion process of the structure of the heterobifunctional monodispersed polyethylene glycol.

Moreover, since the heterobifunctional monodispersed polyethylene glycol of the invention has a monodispersed polyethylene glycol main chain capable of adjusting the chain length, it has a characteristic that decrease in the reactivity owing to the steric hindrance between an antibody and a drug can be avoided without impairing the hydrophilicity of ADC by increasing the monodispersed polyethylene glycol chain length in the bonding of an antibody-linker compound and a drug or a drug-linker compound and an antibody.

Thus, the present invention is as follows.
[1] A heterobifunctional monodispersed polyethylene glycol represented by the formula (1):

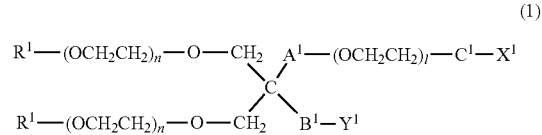

(1)

(in the formula (1), $X^1$ and $Y^1$ are each an atomic group containing at least a functional group capable of forming a covalent bond upon a reaction with a functional group present in a biofunctional molecule, the functional group contained in the atomic group $X^1$ and the functional group contained in the atomic group $Y^1$ are different from each other; $R^1$ is a hydrocarbon group having from 1 to 7 carbon atoms or a hydrogen atom; n is an integer of 3 to 72; l is an integer of 2 to 72; A represents -$L^1$-$(CH_2)_{m1}$— or -$L^1$-$(CH_2)_{m1}$-$L^2$-$(CH_2)_{m2}$—, $L^1$ represents an ether bond, an amide bond, an urethane bond, a secondary amino group or a single bond, $L^2$ represents an amide bond or an urethane bond, and m1 and m2 represent each independently an integer of 1 to 5; $B^1$ represents -$L^3$-$(CH_2)_{m3}$—, -$L^3$-$(CH_2)_{m3}$-$L^4$-$(CH_2)_{m4}$— or a single bond, $L^3$ represents an amide bond or a single bond, $L^4$ represents an ether bond, an amide bond or an urethane bond, and m3 and m4 represent each independently an integer of 1 to 5; and $C^1$ represents -$L^5$-$(CH_2)_{m5}$—, —O—$CH_2$— or a single bond, $L^5$ represents an amide bond, an urethane bond, a secondary amino group or a single bond, and m5 represents an integer of 1 to 5.)

[2] The heterobifunctional monodispersed polyethylene glycol of [1], wherein, in the formula (1), $A^1$ is represented by —NHC(O)—$(CH_2)_{m1}$— or —NHC(O)—$(CH_2)_{m1}$-$L^2$-$(CH_2)_{m2}$—, $B^1$ is represented by —$(CH_2)_{m3}$— or —$(CH_2)_{m3}$-$L^4$-$(CH_2)_{m4}$—, and $C^1$ is represented by -$L^5$-$(CH_2)_{m5}$—, —O—$CH_2$— or a single bond.

[3] The heterobifunctional monodispersed polyethylene glycol of [1], wherein, in the formula (1), $A^1$ is represented by —$CH_2$— or —$CH_2$-$L^2$-$(CH_2)_{m2}$—, $B^1$ is represented by —$CH_2$— or —$CH_2$-$L^4$-$(CH_2)_{m4}$—, and $C^1$ is represented by -$L^5$-$(CH_2)_{m5}$—, —O—$CH_2$— or a single bond.

[4] The heterobifunctional monodispersed polyethylene glycol of [1], wherein, in the formula (1), $A^1$ is represented by —O—$(CH_2)_{m1}$— or —O—$(CH_2)_{m1}$-$L^2$-$(CH_2)_{m2}$—, $B^1$ is represented by —$CH_2$— or —$CH_2$-$L^4$-$(CH_2)_{m4}$—, and $C^1$ is represented by -L-$(CH_2)_{m5}$—, —O—$CH_2$— or a single bond.

[5] The heterobifunctional monodispersed polyethylene glycol of [1], wherein, in the formula (1), A is represented by —C(O)NH—$(CH_2)_{m1}$— or —C(O)NH—$(CH_2)_{m1}$-$L^2$-$(CH_2)_{m2}$—, $B^1$ is represented by —$CH_2$— or —$CH_2$-$L^4$-$(CH_2)_{m4}$—, and $C^1$ is represented by -L-$(CH_2)_{m5}$—, —O—$CH_2$— or a single bond.

[6] The heterobifunctional monodispersed polyethylene glycol of [1], wherein, in the formula (1), $A^1$ is represented by —C(O)NH—$(CH_2)_{m1}$— or —C(O)NH—$(CH_2)_{m1}$-$L^2$-$(CH_2)_{m2}$—, $B^1$ is represented by —C(O)NH—$(CH_2)_{m3}$— or —C(O)NH—$(CH_2)_{m3}$-$L^4$-$(CH_2)_{m4}$—, and $C^1$ is represented by -$L^5$-$(CH_2)_{m5}$—, —O—$CH_2$— or a single bond.

[7] The heterobifunctional monodispersed polyethylene glycol according to any one of [1] to [6], wherein $X^1$ and $Y^1$ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (l), the formula (m), the formula (n) and the formula (o):

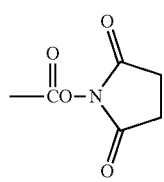
(a)

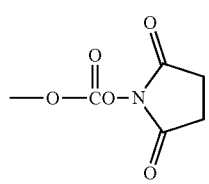
(b1)

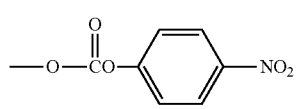
(b2)

(c)

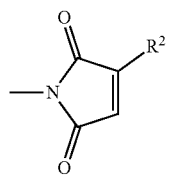
(d)

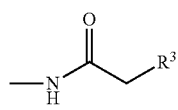
(e)

—COOH (f)

—SH (g)

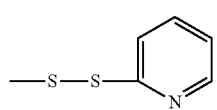
(h)

—NH$_2$ (i)

—O—NH$_2$ (j)

(k)

—C≡C—R$^4$ (l)

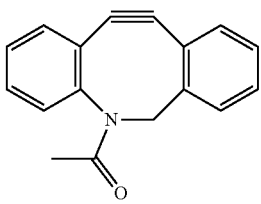
(m)

—N$_3$ (n)

—OH (o)

(in the formula (d), $R^2$ is a hydrogen atom or a hydrocarbon group having from 1 to 5 carbon atoms; in the formula (e), $R^3$ is a halogen atom selected from a chlorine atom, a bromine atom and an iodine atom; and in the formula (1), $R^4$ is a hydrogen atom or a hydrocarbon group having from 1 to 5 carbon atoms.)

[8] An antibody-drug conjugate comprising a heterobifunctional monodispersed polyethylene glycol represented by the formula (2):

$$R^1-(OCH_2CH_2)_n-O-CH_2 \diagdown_C \diagup A^1-(OCH_2CH_2)_l-C^2-X^2 \\ R^1-(OCH_2CH_2)_n-O-CH_2 \diagup^{\phantom{C}} B^2-Y^2 \qquad (2)$$

(in the formula (2), one of $X^2$ and $Y^2$ is an antibody, and other of $X^2$ and $Y^2$ is a drug; $R^1$ is a hydrocarbon group having from 1 to 7 carbon atoms or a hydrogen atom; n is an integer of 3 to 72; l is an integer of 2 to 72; $A^1$ represents -L$^1$-(CH$_2$)$_{m1}$— or -L$^1$-(CH$_2$)$_{m1}$-L$^2$-(CH$_2$)$_{m2}$—, L$^1$ represents an ether bond, an amide bond, an urethane bond, a secondary amino group or a single bond, $L^2$ represents an amide bond or an urethane bond, and m1 and m2 represent each independently an integer of 1 to 5; $B^2$ represents -L$^3$-(CH$_2$)$_{m3}$-L$^6$-, -L$^3$-(CH$_2$)$_{m3}$-L$^4$-(CH$_2$)$_{m4}$-L$^6$- or -L$^6$-, $L^3$ represents an amide bond or a single bond, $L^4$ represents an ether bond, an amide bond or an urethane bond, m3 and m4 represent each independently an integer of 1 to 5, and $L^6$ is an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group or a hydrocarbon group containing any of them; and $C^2$ represents -L$^5$-(CH$_2$)$_{m5}$-L-, —O—CH$_2$-L$^7$- or -L$^7$-, $L^5$ represents an amide bond, an urethane bond, a secondary amino group or a single bond, m5 represents an integer of 1 to 5, and $L^7$ is an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group or a hydrocarbon group containing any of them.)

Effect of the Invention

Since the heterobifunctional monodispersed polyethylene glycol according to the invention does not have a chiral center, a problem of the not-desired partial steric inversion or racemization of the chiral center does not fundamentally occur in the chemical conversion process. Further, since two monodispersed polyethylene glycol side chains are bonded to a quaternary carbon atom of the branched portion by a stable ether bond, it is difficult to be decomposed into a single-chain monodispersed polyethylene glycol in the chemical conversion process. Therefore, an antibody-drug conjugate having high homogeneity can be obtained by linking an antibody and a drug using the heterobifunctional monodispersed polyethylene glycol.

In addition, in the heterobifunctional monodispersed polyethylene glycol, since two monodispersed polyethylene glycol side chains are adjacently bonded to each other, when an antibody-drug conjugate is prepared, the effect of masking the hydrophobic drug is large and thus the occurrence of aggregation or decrease in stability of the antibody in blood caused by the hydrophobicity of the drug can be suppressed.

EMBODIMENTS FOR CARRYING OUT THE INVENTION

Figure 1:
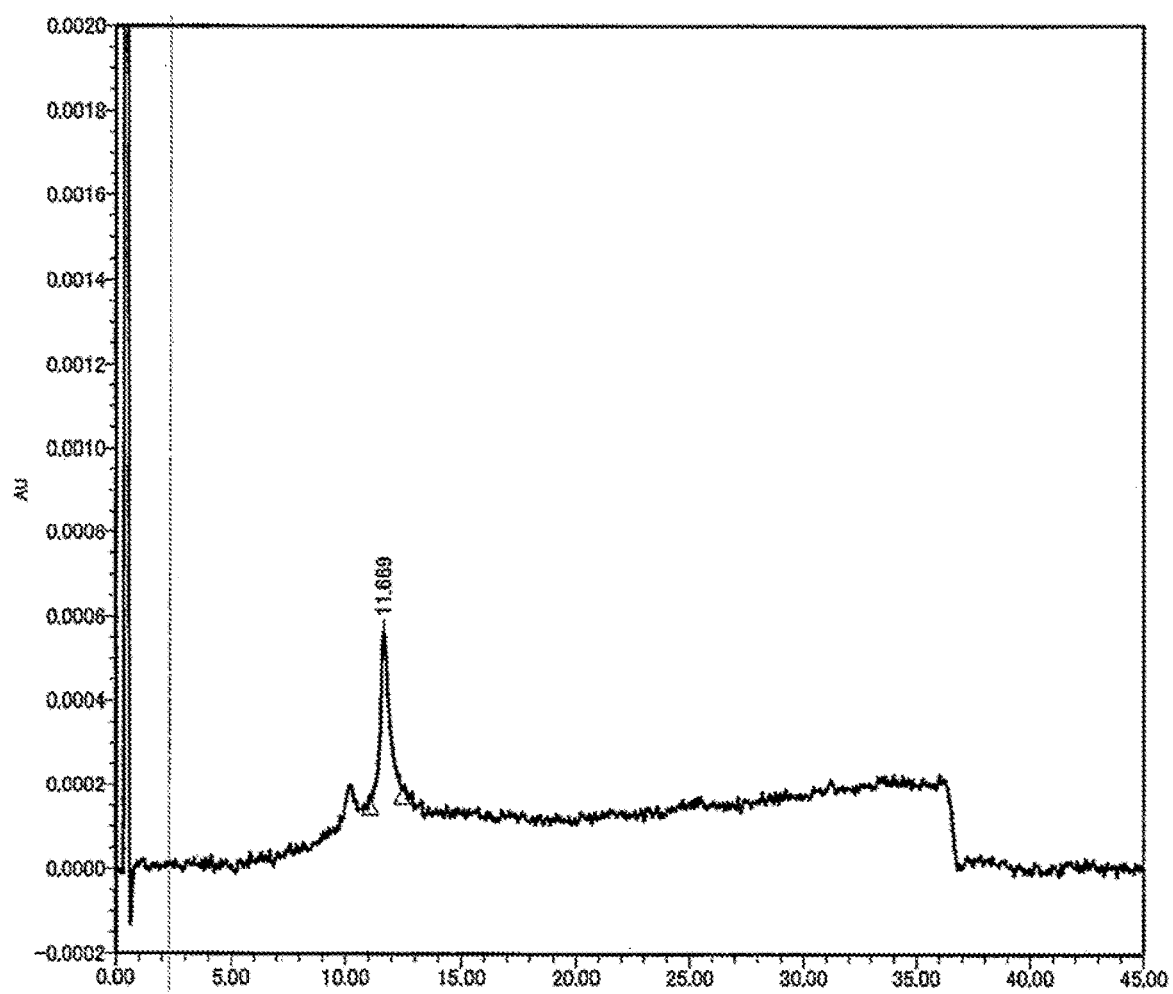
FIG. 1 is a chart of HPLC measurement using a hydrophobic interaction chromatography (HIC) column in Example 8.

The invention will be described in detail below.

In the specification, the "heterobifunctional" means to have two different chemically reactive functional groups, and the "monodispersed polyethylene glycol" referrers to a compound which contains 90% or more of a component having a specific ethylene glycol chain length.

The heterobifunctional monodispersed polyethylene glycol of the invention is represented by the formula (1).

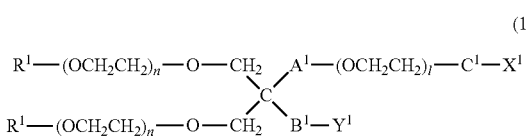

(1)

$R^1$ in the formula (1) of the invention is a hydrocarbon group or a hydrogen atom. The number of carbon atoms of the hydrocarbon group is preferably 7 or less. Examples of the hydrocarbon group include an alkyl group, an aryl group and an aralkyl group, and specific hydrocarbon group includes a methyl group, an ethyl group, a propyl group, an isopropyl group, a tert-butyl group, a phenyl group and a benzyl group. A preferred embodiment of $R^1$ is a methyl group or a hydrogen atom, and more preferably a methyl group.

n in the formula (1) of the invention represents a number of repeating units of monodispersed polyethylene glycol and is an integer of 3 to 72, preferably an integer of 4 to 48, more preferably an integer of 6 to 36, and particularly preferably an integer of 8 to 24.

l in the formula (1) of the invention represents a number of repeating units of monodispersed polyethylene glycol and is an integer of 2 to 72, preferably an integer of 3 to 36, more preferably an integer of 4 to 24, and particularly preferably an integer of 6 to 12. Moreover, l is preferably $1 \leq n$ and further preferably $1 \leq 2n/3$.

In the specification, the atomic groups $X^1$ and $Y^1$ in the formula (1) are different from each other and not particularly limited as long as they are atomic groups containing at least a functional group which reacts with a functional group present in a biofunctional molecule (for example, a physiologically active protein, a peptide, an antibody, a nucleic acid or a low-molecular drug), which is a target for modification by the heterobifunctional monodispersed polyethylene glycol, to form a covalent bond. Examples of the functional group include functional groups described, for example, in "Hermanson, G. T. Bioconjugate Techniques, 2nd ed.; Academic Press: San Diego, CA, 2008", "Harris, J. M. Poly(Ethylene Glycol) Chemistry; Plenum Press: New York, 1992", and "PEGylated Protein Drugs: Basic Science and Clinical Applications; Veronese, F. M., Ed.; Birkhauser: Basel, Switzerland, 2009".

Among them, the functional groups contained in $X^1$ and $Y^1$ are each independently preferably a functional group capable of reacting under mild conditions and with a high reaction efficiency with a functional group (for example, an amino group, a thiol group, an aldehyde group or a carboxyl group) present in a naturally occurring biofunctional molecule represented by protein or a functional group (for example, a maleimide group, a ketone group, an azide group or an alkynyl group) capable of being artificially introduced into the biofunctional molecule described above. More specifically, it is preferably an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, a hydroxy group, an alkynyl group, an allyl group, a vinyl group, an amino group, an oxyamino group, a hydrazide group, an azide group or a dibenzocyclooctyne (DBCO) group. Further, taking the reaction efficiency into consideration, it is preferably an active ester group, an active carbonate group, a maleimide group, an α-haloacetyl group, an alkynyl group, an azide group or a dibenzocyclooctyne (DBCO) group.

In still more specifically, the functional groups contained in $X^1$ and $Y^1$ are each independently preferably an active ester group, an active carbonate group, an aldehyde group, an isocyanate group, an isothiocyanate group, an epoxy group, a maleimide group, a vinyl sulfone group, an acryl group, an α-haloacetyl group, a sulfonyloxy group or a carboxy group in the case where the functional group present in the biofunctional molecule as the target for modification is an amino group; preferably an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, an alkynyl group, an allyl group or a vinyl group in the case where the functional group present in the biofunctional molecule as the target for modification is a thiol group; preferably a thiol group, a hydroxy group, an amino group, an oxyamino group or a hydrazide group in the case where the functional group present in the biofunctional molecule as the target for modification is an aldehyde group or a carboxy group; preferably a thiol group, an amino group, an oxyamino group, a hydrazide group or an azide group in the case where the functional group present in the biofunctional molecule as the target for modification is an alkynyl group; preferably an alkynyl group or a dibenzocyclooctyne (DBCO) group in the case where the functional group present in the biofunctional molecule as the target for modification is an azide group; and preferably a thiol group, a hydroxy group or an amino group in the case where the functional group present in the biofunctional molecule as the target for modification is a halogenated alkyl group, an alkylsulfonic acid eater or an arylsulfonic acid ester.

Here, the "active ester group" indicates an activated carboxy group represented by the formula: —C(=O)-L, wherein L represents a leaving group. The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The "active carbonate" indicates an activated carbonate group represented by the formula: —O—C(=O)-L, wherein L represents a leaving group the same as that described above.

In a preferred embodiment of the invention, $X^1$ and $Y^1$ are each independently a group represented by Group (I), Group (II), Group (III), Group (IV), Group (V) or Group (VI).

Group (I): A functional group capable of forming a covalent bond upon a reaction with an amino group of the biofunctional molecule
The following (a), (b1), (b2), (c), (d), (e) and (f):

Group (II): A functional group capable of forming a covalent bond upon a reaction with a thiol group of the biofunctional molecule
The following (a), (b1), (b2), (c), (d), (e), (f), (g), (h) and (1):

Group (III): A functional group capable of forming a covalent bond upon a reaction with an aldehyde group or a carboxy group of the biofunctional molecule
The following (g), (i), (j), (k) and (o):

Group (IV): A functional group capable of forming a covalent bond upon a reaction with an alkynyl group of the biofunctional molecule
The following (g), (i), (j), (k) and (n):

Group (V): A functional group capable of forming a covalent bond upon a reaction with an azide group of the biofunctional molecule
The following (1) and (m):

Group (VI): A functional group capable of forming a covalent bond upon a reaction with a halogenated alkyl group, an alkylsulfonic acid ester or an arylsulfonic acid ester of the biofunctional molecule
The following (g), (i) and (o).

In the preferred embodiment of the invention, $X^1$ and $Y^1$ are each independently particularly preferably the groups (a) to (n).

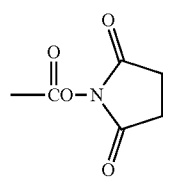
(a)

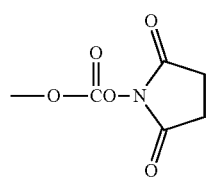
(b1)

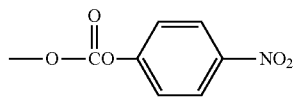
(b2)

(c)

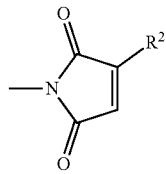
(d)

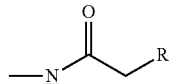
(e)

—COOH (f)

—SH (g)

(h)

—NH$_2$ (i)

—O—NH$_2$ (j)

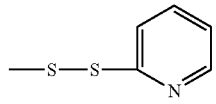
(k)

—C≡C—R$^4$ (l)

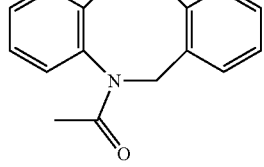
(m)

—N$_3$ (n)

—OH (o)

In the formulae, $R^2$ and $R^4$ are each a hydrogen atom or a hydrocarbon group having from 1 to 5 carbon atoms, and example of the hydrocarbon group include an alkyl group, and specific hydrocarbon group includes a methyl group, an ethyl group, a propyl group, an isopropyl group, a butyl group, a tert-butyl group and a pentyl group. $R^3$ is a halogen atom selected from a chlorine atom, a bromine atom and an iodine atom.

As to preferred combinations of the functional groups contained in the atomic groups $X^1$ and $Y^1$ in the formula (1), when the functional group contained in $X^1$ is an active ester group or an active carbonate group, the functional group contained in $Y^1$ is a group selected from a maleimide group, a vinyl sulfone group, an α-haloacetyl group, an alkynyl group, a dibenzocyclooctyne (DBCO) group and an azide group; when the functional group contained in $X^1$ is an aldehyde group, the functional group contained in $Y^1$ is a group selected from a maleimide group, a vinyl sulfone group, an alkynyl group, a dibenzocyclooctyne (DBCO) group and an azide group; when the functional group contained in $X^1$ is a maleimide group, a vinyl sulfone group or an α-haloacetyl group, the functional group contained in $Y^1$ is a group selected from an active ester group, an active carbonate group, an alkynyl group, a dibenzocyclooctyne (DBCO) group and an azide group; when the functional group contained in $X^1$ is an alkynyl group, a dibenzocyclooctyne (DBCO) group or an azide group, the functional group contained in $Y^1$ is a group selected from a maleimide group, a vinyl sulfone group, an α-haloacetyl group, an active ester group, an active carbonate group, an amino group, an oxyamino group and a hydroxy group; when the functional group contained in $X^1$ is an amino group or an oxyamino group, the functional group contained in $Y^1$ is an alkynyl group, a dibenzocyclooctyne (DBCO) group, an azide group, a thiol group, a hydroxy group or a carboxy group; and when the functional group contained in $X^1$ is a thiol group, a 2-pyridyldithio group or a hydroxy group, $Y^1$ is a group selected from an amino group, an oxyamino group, an azide group and a carboxy group. More preferably, when the functional group contained in $X^1$ is an active ester group or an active carbonate group, the functional group contained in $Y^1$ is a group selected from a maleimide group, an α-haloacetyl group, an alkynyl group, a dibenzocyclooctyne (DBCO) group and an azide group; when the functional group contained in $X^1$ is an aldehyde group, the functional group contained in $Y^1$ is a group selected from a maleimide group, an α-haloacetyl group, an alkynyl group, a dibenzocyclooctyne (DBCO) group and an azide group; when the functional group contained in $X^1$ is a maleimide group or an α-haloacetyl group, the functional group contained in $Y^1$ is a group selected from an active ester group, an active carbonate group, an alkynyl group, a dibenzocyclooctyne (DBCO) group and an azide group; when the functional group contained in $X^1$ is an alkynyl group, a dibenzocyclooctyne (DBCO) group or an azide group, the functional group contained in $Y^1$ is a group selected from a maleimide group, an α-haloacetyl group, an active ester group, an active carbonate group, an amino group, an oxyamino group and a hydroxy group; when the functional group contained in $X^1$ is an amino group or an oxyamino group, the functional group contained in $Y^1$ is an alkynyl group, a dibenzocyclooctyne (DBCO) group, an azide group, a hydroxy group or a thiol group; and when the functional group contained in $X^1$ is a thiol group, a 2-pyridyldithio group or a hydroxy group, the functional group contained in $Y^1$ is a group selected from an amino group, an oxyamino group and an azide group.

$A^1$ in the formula (1) of the invention is a divalent spacer between a quaternary carbon atom of the branched portion and the monodispersed polyethylene glycol bonded to $X^1$, $B^1$ in the formula (1) is a divalent spacer between the quaternary carbon atom of the branched portion and $Y^1$, $C^1$ in the formula (1) of the invention is a divalent spacer between the monodispersed polyethylene glycol bonded to $A^1$ and $X^1$, and these are composed of a covalent bond, respectively. Specifically, $A^1$ represents -$L^1$-$(CH_2)_{m1}$— or -$L^1$-$(CH_2)_{m1}$-$L^2$-$(CH_2)_{m2}$—, $L^1$ represents an ether bond, an amide bond, an urethane bond, a secondary amino group or a single bond, $L^2$ represents an amide bond or an urethane bond, and m1 and m2 represent each independently an integer of 1 to 5. $B^1$ represents -$L^3$-$(CH_2)_{m3}$—, -$L^3$-$(CH_2)_{m3}$-$L^4$-$(CH_2)_{m4}$— or a single bond, $L^3$ represents an amide bond or a single bond, $L^4$ represents an ether bond, an amide bond or an urethane bond, and m3 and m4 represent each independently an integer of 1 to 5. $C^1$ represents -$L^5$-$(CH_2)_{m5}$—, —O—$CH_2$— or a single bond, $L^5$ represents an amide bond, an urethane bond, a secondary amino group or a single bond, and m5 represents an integer of 1 to 5.

Specific structures of $A^1$, $B^1$ and $C^1$ in the formula (1) in preferred embodiments of the invention and typical synthesis examples of the heterobifunctional monodispersed polyethylene glycol having $A^1$, $B^1$ and $C^1$ described above are described below, but the invention should not be construed as being limited thereto.

(A) In a preferred embodiment of the invention, $A^1$ in the formula (1) is represented by —NHC(O)—$(CH_2)_{m1}$— or —NHC(O)—$(CH_2)_{m1}$-$L^2$-$(CH_2)_{m2}$—, $L^2$ is an amide bond or an urethane bond, and m1 and m2 are each independently an integer of 1 to 5, $B^1$ is represented by —$(CH_2)_{m3}$— or —$(CH_2)_{m3}$-$L^4$-$(CH_2)_{m4}$—, $L^4$ is an ether bond, an amide bond or an urethane bond, and m3 and m4 are each independently an integer of 1 to 5, and $C^1$ is represented by -$L^5$-$(CH_2)_{m5}$—, —O—$CH_2$— or a single bond, $L^5$ is an amide bond, an urethane bond, a secondary amino group or a single bond, and m5 is an integer of 1 to 5. More preferably, $A^1$ is represented by —NHC(O)—$(CH_2)_{m1}$—, and m1 is an integer of 1 to 5, $B^1$ is represented by —$(CH_2)_{m3}$— or —$(CH_2)_{m3}$—O—$(CH_2)_{m4}$—, and m3 and m4 are each independently an integer of 1 to 5, and $C^1$ is represented by —NHC(O)—$(CH_2)_{m5}$— or a single bond and m5 is an integer of 1 to 5.

Typical example of synthesis of the heterobifunctional monodispersed polyethylene glycol described above includes the steps described below. Here, a compound into which a maleimide group and a p-nitrophenyl carbonate group are introduced as the functional groups is illustrated.

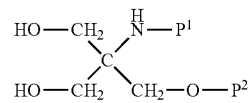

(3)

(in the formula (3), $P^1$ is a protective group of an amino group, and $P^2$ is a protective group of a hydroxy group.)

The compound represented by the formula (3) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by the formula (4) shown below.

The "protective group" as referred to herein is a component which prevents or blocks a reaction of a specific functional group in the molecule under certain reaction conditions. The protective group varies depending on the kind of the functional group to be protected, the conditions to be used and the presence of the other functional group or protective group in the molecule. Specific examples of the protective group can be found in many general books and are described, for example, in "Wuts, P. G M.; Greene, T. W. Protective Groups in Organic Synthesis, 4th ed.; Wiley-Interscience. New York, 2007". Moreover, as to the functional group protected by the protective group, the original functional group can be reproduced by deprotection using reaction conditions suitable for each of the protective groups, that is, causing a chemical reaction. The representative deprotection conditions of the protective group are described in the literature described above.

As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group.

When the functional group to be protected is a carboxy group, for example, an alkyl ester-based protective group and a silyl ester-based protective group are exemplified, and specific examples thereof include a methyl group, a 9-fluorenylmethyl group and a tert-butyldimethylsilyl group. When the functional group to be protected is a sulfanyl group, for example, a thioether-based protective group, a thiocarbonate-based protective group and a disulfide-based protective group are exemplified, and specific examples thereof include an S-2,4-dinitrophenyl group, an S-9-fluorenylmethyloxycarbonyl group and an S-tert-butyldisulfide group. Further, a bifunctional protective group capable of simultaneously protecting two functional groups of the same kinds or different kinds may be used. As to preferred combinations of the functional groups to be protected and the protective group, when the functional groups to be protected are two hydroxy groups, for example, a cyclic acetal-based protective group and a cyclic silyl-based protective group are mentioned, and specific examples thereof include a 2,2-dimethyl-1,3-dioxolane group, a 2,2-dimethyl-1,3-dioxane group, a 2-phenyl-1,3-dioxolane group, a 2-phenyl-1,3-dioxane group and a di-tert-butylsilylene group. When the functional groups to be protected are an amino group and a hydroxy group, for example, an oxazoline-based protective group is exemplified, and specific examples thereof include a 2-phenyloxazoline group.

The representative deprotection conditions of the protective group are described in the literature described above, and the reaction conditions suitable for each of the protective groups can be selected. However, in the case where the functional group contained in the structure is a functional group which does not inhibit the chemical reaction of other functional group even when the functional group is not protected by a protective group, it is not necessary to use a protective group.

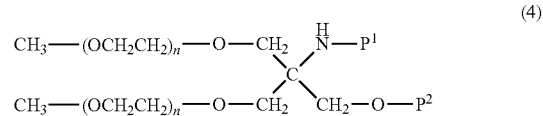

(4)

After deprotecting the protective group $P^1$ of the compound represented by the formula (4) described above, the resulting compound is reacted with a maleimidopropionic acid amide of monocarboxy monodispersed polyethylene glycol in the presence of a condensing agent to obtain a compound represented by the formula (5) shown below. Here, when the reaction conditions in which the hydroxy group does not react with a reaction reagent of the amino group are selected, the protective group $P^2$ may also be deprotected simultaneously with the protective group $P^1$.

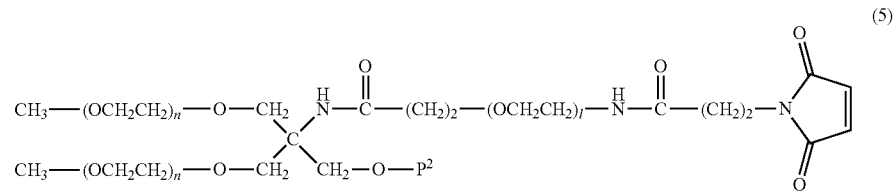

(5)

After deprotecting the protective group $P^2$ of the compound represented by the formula (5) described above, the resulting compound is reacted with p-nitrophenyl chloroformate in the presence of a base to obtain a compound represented by the formula (6) shown below.

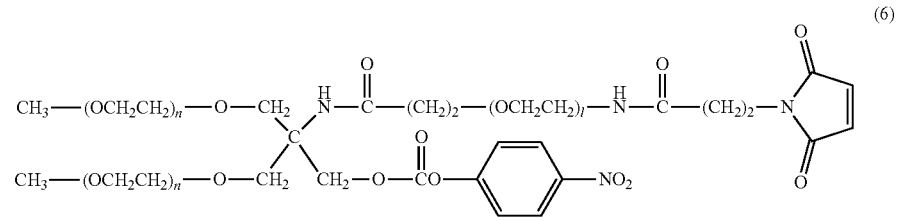

(6)

(B) In another preferred embodiment of the invention, A in the formula (1) is represented by —$CH_2$— or —$CH_2$-$L^2$-($CH_2$)$_{m2}$—, $L^2$ is an amide bond or an urethane bond, and m2 is an integer of 1 to 5, $B^1$ is represented by —$CH_2$— or —$CH_2$-$L^4$-($CH_2$)$_{m4}$—, $L^4$ is an ether bond, an amide bond or an urethane bond, and m4 is an integer of 1 to 5, and $C^1$ represents -$L^5$-($CH_2$)$_{m5}$—, —O—$CH_2$— or a single bond, $L^5$ is an amide bond, an urethane bond, a secondary amino group or a single bond, and m5 is an integer of 1 to 5. More preferably, $A^1$ is represented by —$CH_2$—NHC(O)—($CH_2$)$_{m2}$—, and m2 is an integer of 1 to 5, $B^1$ is represented by —$CH_2$— or —$CH_2$—O—($CH_2$)$_{m4}$—, and m4 is an integer of 1 to 5, and $C^1$ is represented by —NHC(O)—($CH_2$)$_{m5}$— or a single bond and m5 is an integer of 1 to 5.

Typical example of synthesis of the heterobifunctional monodispersed polyethylene glycol described above includes the steps described below. Here, a compound into which an bromoacetamide group and an N-succinimidyl ester group are introduced as the functional groups is illustrated.

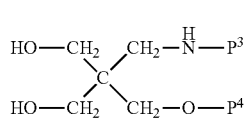

(7)

(in the formula (7), $P^3$ is a protective group of an amino group, and $P^4$ is a protective group of a hydroxy group.)

The compound represented by the formula (7) described above is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by the formula (8) shown below.

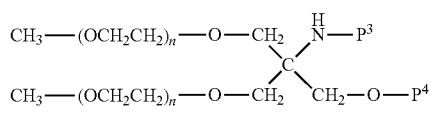

(8)

After deprotecting the protective group $P^4$ of the compound represented by the formula (8) described above, the resulting compound is reacted with a carboxy group-protected body of 4-hydroxybutanoic acid in an anhydrous solvent in the presence of a base to obtain a compound represented by the formula (9) shown below.

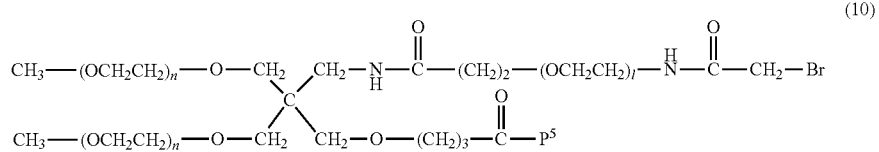

(9)

(in the formula, $p^5$ is a protective group of a carboxy group.)

After deprotecting the protective group $P^3$ of the compound represented by the formula (9) described above, the resulting compound is reacted with tetrafluorophenyl ester of monobromoacetamido monodispersed polyethylene glycol to obtain a compound represented by the formula (10) shown below.

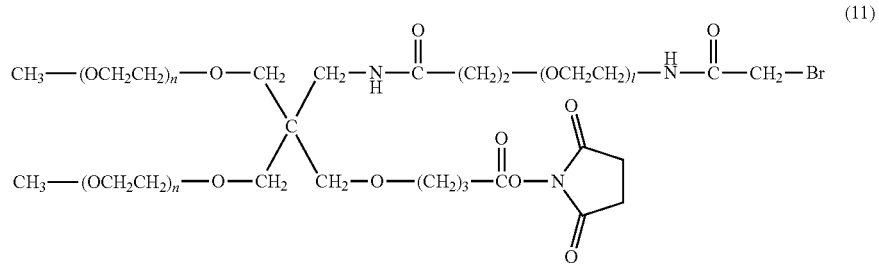

(10)

After deprotecting the protective group $P^5$ of the compound represented by the formula (10) described above, the resulting compound is reacted with N-hydroxysuccinimide in the presence of a condensing agent to obtain a compound represented by the formula (11) shown below.

(11)

(C) In still another preferred embodiment of the invention, $A^1$ in the formula (1) is represented by —O—$(CH_2)_{m1}$— or —O—$(CH_2)_{m1}$-$L^2$-$(CH_2)_{m2}$—, $L^2$ is an amide bond or an urethane bond, and m1 and m2 are each independently an integer of 1 to 5, $B^1$ is represented by —$CH_2$— or —$CH_2$-$L^4$-$(CH_2)_{m4}$—, $L^4$ is an ether bond, an amide bond or an urethane bond, and m4 is an integer of 1 to 5, and CP represents -$L^5$-$(CH_2)_{m5}$—, —O—$CH_2$— or a single bond, $L^5$ is an amide bond, an urethane bond, a secondary amino group or a single bond, and m5 is an integer of 1 to 5. More preferably, $A^1$ is represented by —O—$(CH_2)_{m1}$—NHC(O)—NH—$(CH_2)_{m2}$—, and m1 and m2 are each independently an integer of 1 to 5, $B^1$ is represented by —$CH_2$— or —$CH_2$—O—$(CH_2)_{m4}$— and m4 is an integer of 1 to 5, and CH is represented by —NHC(O)—$(CH_2)_{m5}$— or a single bond and m5 is an integer of 1 to 5.

Typical example of synthesis of the heterobifunctional monodispersed polyethylene glycol described above includes the steps described below. Here, a compound into which a 2-pyridyldithio group and an N-succinimidyl carbonate group are introduced as the functional groups is illustrated.

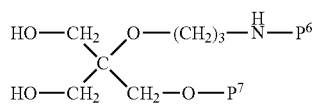
(12)

(in the formula (12), $P^6$ is a protective group of an amino group, and $P^7$ is a protective group of a hydroxy group.)

The compound represented by the formula (12) described above is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by the formula (13) shown below.

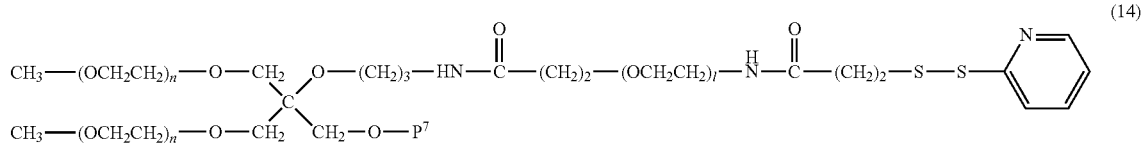
(13)

After deprotecting the protective group $P^6$ of the compound represented by the formula (13) described above, the resulting compound is reacted with 3-(2-pyridyldithio)propionamide of monocarboxy monodispersed polyethylene glycol in the presence of a condensing agent to obtain a compound represented by the formula (14) shown below.

(14)

After deprotecting the protective group $P^7$ of the compound represented by the formula (14) described above, the resulting compound is reacted with N,N'-disuccinimidyl carbonate in the presence of a base to obtain a compound represented by the formula (15) shown below.

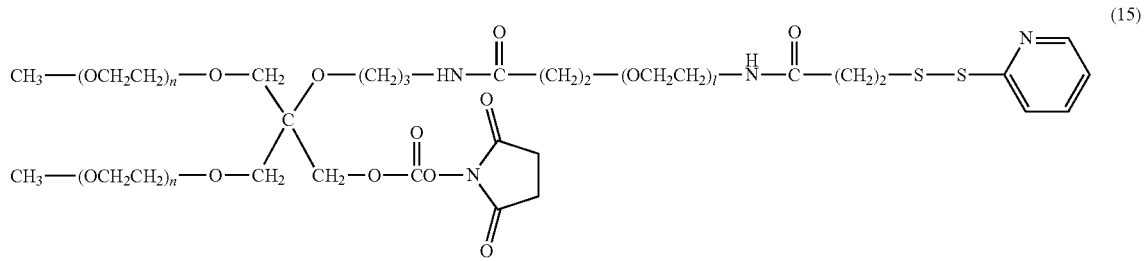
(15)

(D) In a further preferred embodiment of the invention, A in the formula (1) is represented by —C(O)NH—$(CH_2)_{m1}$— or —C(O)NH—$(CH_2)_{m1}$-$L^2$-$(CH_2)_{m2}$—, $L^2$ is an amide bond or an urethane bond, and m1 and m2 are each independently an integer of 1 to 5, $B^1$ is represented by —$CH_2$— or —$CH_2$-$L^4$-$(CH_2)_{m4}$—, $L^4$ is an ether bond, an amide bond or an urethane bond, and m4 is an integer of 1 to 5, and $C^1$ is represented by -$L^5$-$(CH_2)_{m5}$—, —O—$CH_2$— or a single bond, $L^5$ is an amide bond, an urethane bond, a secondary amino group or a single bond, and m5 is an integer of 1 to 5. More preferably, $A^1$ is represented by —C(O)NH—$(CH_2)_{m1}$—, and m1 is an integer of 1 to 5, $B^1$ is represented by $CH_2$— or —$CH_2$—O—$(CH_2)_{m4}$— and m4 is an integer of 1 to 5, and $C^1$ is represented by —C(O)NH—$(CH_2)_{m5}$— or a single bond and m5 is an integer of 1 to 5.

Typical example of synthesis of the heterobifunctional monodispersed polyethylene glycol described above includes the steps described below. Here, a compound into which an azide group and a p-nitrophenyl carbonate group are introduced as the functional groups is illustrated.

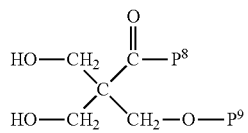

(16)

(in the formula (16), $P^8$ is a protective group of a carboxy group, and $P^9$ is a protective group of a hydroxy group.)

The compound represented by the formula (16) is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by the formula (17) shown below.

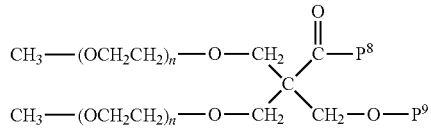

(17)

After deprotecting the protective group P of the compound represented by the formula (17) described above, the resulting compound is reacted with an azide of monoamino monodispersed polyethylene glycol in the presence of a condensing agent to obtain a compound represented by the formula (18) shown below.

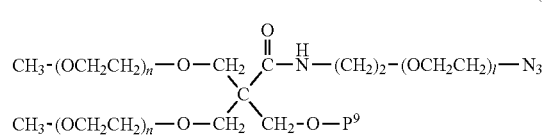

(18)

After deprotecting the protective group $P^9$ of the compound represented by the formula (18) described above, the resulting compound is reacted with p-nitrophenyl chloroformate in the presence of a base to obtain a compound represented by the formula (19) shown below.

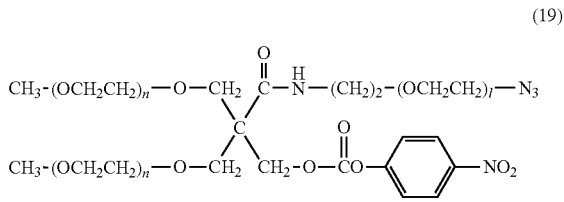

(19)

(E) In a still further preferred embodiment of the invention, $A^1$ in the formula (1) is represented by —C(O)NH—$(CH_2)_{m1}$— or —C(O)NH—$(CH_2)_{m1}$-$L^2$-$(CH_2)_{m2}$—, $L^2$ is an amide bond or an urethane bond, and m1 and m2 are each independently an integer of 1 to 5, $B^1$ is represented by —C(O)NH—$(CH_2)_{m3}$— or —C(O)NH—$(CH_2)_{m3}$-$L^4$-$(CH_2)_{m4}$—, $L^4$ is an ether bond, an amide bond or an urethane bond, and m3 and m4 are each independently an integer of 1 to 5, and $C^1$ is represented by -$L^5$-$(CH_2)_{m5}$—, —O—$CH_2$— or a single bond, $L^5$ is an ether bond, an amide bond, an urethane bond, a secondary amino group or a single bond, and m5 is an integer of 1 to 5. More preferably, $A^1$ is represented by —C(O)NH—$(CH_2)_{m1}$— and m1 is an integer of 1 to 5, $B^1$ is represented by —C(O)NH—$(CH_2)_{m3}$—NHC(O)—$(CH_2)_{m4}$—, and m3 and m4 are each independently an integer of 1 to 5, and $C^1$ is represented by —C(O)NH—$(CH_2)_{m5}$— or a single bond and m5 is an integer of 1 to 5.

Typical example of synthesis of the heterobifunctional monodispersed polyethylene glycol described above includes the steps described below. Here, a compound into which a dibenzocyclooctyne (DBCO) group and a maleimide group are introduced as the functional groups is illustrated.

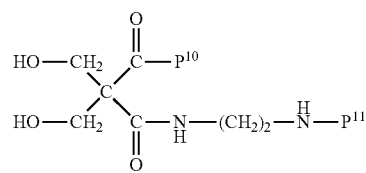

(20)

(in the formula (20), $P^{10}$ is a protective group of a carboxy group, and $P^{11}$ is a protective group of an amino group.)

The compound represented by the formula (20) described above is subjected to a nucleophilic substitution reaction with an alkyl or aryl sulfonic acid ester of monomethyl monodispersed polyethylene glycol or a halide of monomethyl monodispersed polyethylene glycol in an anhydrous solvent in the presence of a strong base to obtain a compound represented by the formula (21) shown below.

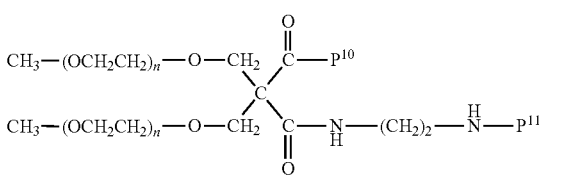

(21)

After deprotecting the protective group $P^{10}$ of the compound represented by the formula (21) described above, the resulting compound is reacted with a dibenzocyclooctyne (DBCO) derivative of monoamino monodispersed polyethylene glycol in the presence of a condensing agent to obtain a compound represented by the formula (22) shown below.

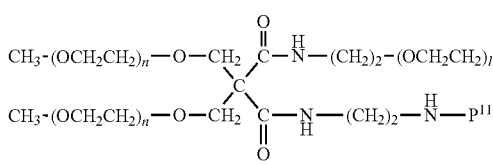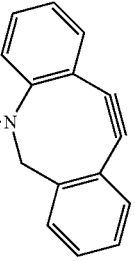

(22)

After deprotecting the protective group $P^{11}$ of the compound represented by the formula (22) described above, the resulting compound is reacted with N-succinimidyl 3-maleimidopropionate to obtain a compound represented by the formula (23) shown below.

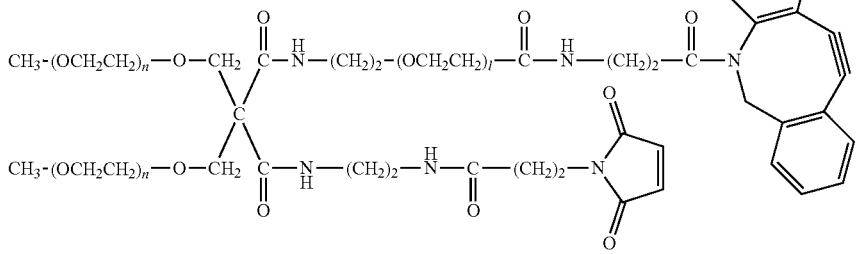

(23)

According to another aspect of the invention, an antibody-drug conjugate containing the heterobifunctional monodispersed polyethylene glycol represented by the formula (2) is provided.

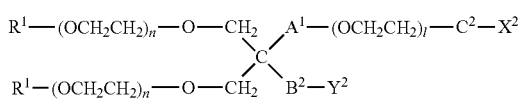

(2)

$R^1$ in the formula (2) of the invention is a hydrocarbon group or a hydrogen atom. The number of carbon atoms of the hydrocarbon group is preferably 7 or less. Examples of the hydrocarbon group include an alkyl group, an aryl group and an aralkyl group, and specific hydrocarbon group includes a methyl group, an ethyl group, a propyl group, an isopropyl group, a tert-butyl group, a phenyl group and a benzyl group. A preferred embodiment of $R^1$ is a methyl group or a hydrogen atom, and more preferably a methyl group.

n in the formula (2) of the invention represents a number of repeating units of monodispersed polyethylene glycol and is an integer of 3 to 72, preferably an integer of 4 to 48, more preferably an integer of 6 to 36, and particularly preferably an integer of 8 to 24.

1 in the formula (2) of the invention represents a number of repeating units of monodispersed polyethylene glycol and is an integer of 2 to 72, preferably an integer of 3 to 36, more preferably an integer of 4 to 24, and particularly preferably an integer of 6 to 12. Further, 1 is preferably 1≤n and further preferably 1≤2n/3.

In the specification, one of $X^2$ and $Y^2$ in the formula (2) is an antibody and the other is a drug.

The term "antibody" as used in the specification is used in its broadest sense and specifically covers a monoclonal antibody, a polyclonal antibody, a dimer, a multimer, a multispecific antibody (for example, a bispecific antibody) and an antibody fragment, as far as it exhibits the desired biological activity (Miller, K. et al. J. Immunol. 2003, 170, 4854-4861).

The antibody can be a mouse antibody, a human antibody, a humanized antibody or a chimeric antibody, or can be derived from other species. The antibody is a protein generated by the immune system, which is capable of recognizing and binding to a specific antigen (Janeway, C.; Travers, P.; Walport, M.; Shlomchik, M. Immunobiology, 5th ed.; Garland Publishing: New York, 2001). A target antigen generally has numerous binding sites (also called epitopes) recognized by CDRs on multiple antibodies. An antibody which specifically binds to a different epitope has a different structure. Therefore, one antigen may have more than one corresponding antibody. The antibody includes the full-length immunoglobulin molecule or an immunologically active portion of a full-length immunoglobulin molecule (that is, a molecule containing an antigen binding site which immunospecifically binds to an antigen of interest or part thereof). Such a target includes a cancer cell and a cell which generates an autoimmune antibody associated with an autoimmune disease, but it is not limited thereto. The immunoglobulin disclosed in the specification may be of any type (for example, IgG, IgE, IgM, IgD or IgA), class (for example, IgG1, IgG2, IgG3, IgG4, IgA1 or IgA2) or subclass of the immunoglobulin molecule. The immunoglobulin may be derived from any species. However, in one embodiment, the immunoglobulin is of human origin, mouse origin or rabbit origin.

The polyclonal antibody is a heterogeneous population of antibody molecules, for example, one derived from the serum of an immunized animal. The polyclonal antibody to an antigen of interest may be produced using known various procedures in the art. For example, in order to produce a polyclonal antibody, various host animals including, but not limited to, rabbit, mouse, rat and guinea pig, may be immunized by injection with an antigen of interest or derivative thereof. The immunological response may be increased by using various adjuvants including, but not limited to, Freund's (complete and incomplete) adjuvant, a mineral gel such as aluminum hydroxide, a surface active substance such as lysolecithin, a pluronic polyol, a polyanion, a peptide, an oil emulsion, keyhole limpet hemocyanin, dinitrophenol, and a potentially useful human adjuvant such as BCG (Bacille Calmett-Guerin) or *Corynebacterium parvum*, depending on the host species. Such adjuvants are also known in the art.

The monoclonal antibody is a homogeneous population of antibodies to a specific antigenic determinant (for example, a cell antigen (cancer or autoimmune cell antigen), a viral antigen, a microbial antigen, a protein, a peptide, a carbohydrate, a chemical substance, a nucleic acid or antigen-binding fragments thereof). A monoclonal antibody (mAb) to an antigen of interest may be prepared by using any technique known in the art. These include, but are not limited to, the hybridoma technique originally described by Kohler, G; Milstein, C. Nature 1975, 256, 495-497, the human B cell hybridoma technique (Kozbor, D. et al. Immunol. Today 1983, 4, 72-79) and the EBV-hybridoma technique (Cole, S. P. C. et al. Monoclonal Antibodies and Cancer Therapy; Alan R. Liss: New York, 1985, pp. 77-96). Such antibodies may be of any immunoglobulin class including IgG, IgM, IgE, IgA and IgD and any subclass thereof. The hybridoma producing the monoclonal antibody in the invention may be cultivated in vitro or in vivo.

The monoclonal antibody includes, but is not limited to, a human monoclonal antibody, a humanized monoclonal antibody, a chimeric monoclonal antibody and an antibody fragment. The human monoclonal antibody may be made by any of numerous techniques known in the art (see, for example, Teng, N. N. et al. Proc. Natl. Acad. Sci. USA. 1983, 80, 7308-7312, Kozbor, D. et al. Immunology Today 1983, 4, 72-79, Olsson L. et al. Meth. Enzymol. 1982, 92, 3-16, and U.S. Pat. Nos. 5,939,598 and 5,770,429). Are combinant antibody, for example, a chimeric monoclonal antibody or a humanized monoclonal antibody can be made using standard recombinant DNA techniques known in the art (see, for example, U.S. Pat. Nos. 4,816,567 and 4,816,397).

The immunogenicity of the antibody can also be reduced by the surface reconstruction (resurfacing) treatment of the antibody (see, U.S. Pat. No. 5,225,539 and European Patent Nos. 0239400, 0519596 and 0592106).

In one embodiment of the invention, the antibody may be a bispecific antibody. Methods for making the bispecific antibody are known in the art. Conventional production method of full-length bispecific antibody utilizes the simultaneous expression of two immunoglobulin heavy chain-light chain pairs in which the two chains have different specificities (see, Milstein, C. et al. Nature 1983, 305, 537-539). According to a different method, the bispecific antibody can also be produced by fusing an antibody variable domain having the desired binding specificity (antibody-antigen binding site) to an immunoglobulin constant domain sequence.

Other useful antibodies include fragments of antibodies, but are not limited to, F(ab')2 fragment, Fab' fragment, Fab fragment, Fvs, a single chain antibody (SCA) (for example, as described in U.S. Pat. No. 4,946,778, Bird, R. E. et al. Science 1988, 242, 423-442, Huston, J. S. et al. Proc. Natl. Acad. Sot USA 1988, 85, 5879-5883, and Ward, E. S. et al. Nature 1989, 334, 544-554), scFv, sc-Fv-Fc, FvdsFv, minibody, diabody, triabody, tetrabody, and any other molecule containing CDR and having the same specificity as the antibody, for example, a domain antibody.

In a preferred embodiment of the invention, a known antibody for the treatment or prevention of cancer may be used. All target proteins including any target protein whose expression is correlated with expression on cells of a cancer, cell proliferative disorder or tumor can be made a target of the antibody.

In a preferred embodiment of the invention, the antibody is useful for the treatment of cancer. Examples of the antibody useful for the treatment of cancer include, but are not limited to, Rituxan (registered trademark) (Genentech Inc.) which is a chimeric anti-CD20 monoclonal antibody for the treatment of a patient with non-Hodgkin's lymphoma, OvaRex (AltaRex Corp.) which is a mouse antibody for the treatment of ovarian cancer, Panorex (Glaxo Wellcome Inc.) which is a mouse IgG2a antibody for the treatment of colorectal cancer, Cetuximab Erbix (ImClone Systems Inc.) which is an anti-EGFR IgG chimeric antibody for the treatment of epidermal growth factor positive cancer, for example, head cancer or neck cancer, Vitaxin (MedImmune Inc.) which is a humanized antibody for the treatment of sarcoma, Campath I/H (Leukosite Inc.) which is a humanized IgG1 antibody for the treatment of chronic lymphocytic leukemia (CLL), Smart M 195 (Protein Design Labs Inc.) which is a humanized anti-CD33 IgG antibody for the treatment of acute myeloid leukemia (AML), Lymphocide (Immunomedics Inc.) which is a humanized anti-CD22 IgG antibody for the treatment of non-Hodgkin's lymphoma, Smart ID 10 (Protein Design Labs Inc.) which is a humanized anti-HLA-DR antibody for the treatment of non-Hodgkin's lymphoma, Oncolym (Techniclone Inc.) which is a radiolabeled mouse anti-HLA-Dr10 antibody for the treatment of non-Hodgkin's lymphoma, AlloMune (BioTransplant Inc.) which is a humanized anti-CD2 mAb for the treatment of Hodgkin's disease or non-Hodgkin's lymphoma, Avastin (Genentech Inc.) which is an anti-VEGF humanized antibody for the treatment of lung cancer and colorectal cancer, Epratuzamab (Immunomedics Inc. and Amgen Inc.) which is an anti-CD22 antibody for the treatment of non-Hodgkin's lymphoma, and CEAcide (Immunomedics Inc.) which is a humanized anti-CEA antibody for the treatment of colorectal cancer.

In a preferred embodiment of the invention, the antibody is an antibody to the following antigens: CA125, CA15-3, CA19-9, L6, Lewis Y, Lewis X, alpha fetoprotein, CA242, placental alkaline phosphatase, prostate specific membrane antigen, EphB2, TMEFF2, prostatic acid phosphatase, epidermal growth factor, MAGE-1, MAGE-2, MAGE-3, MAGE-4, anti-transferrin receptor, p97, MUC1-KLH, CEA, gp 100, MART 1, prostate specific antigen, IL-2 receptor, CD20, CD52, CD33, CD22, human chorionic gonadotropin, CD38, CD40, mucin, P21, MPG and Neu oncogene product. Some specific useful antibodies include, but are not limited to, mAb to the CD40 antigen, for example, BR96 mAb (Trail, P. A. et al. Science 1993, 261, 212-215), BR64 (Trail, P. A. et al. Cancer Research 1997, 57, 100-105) or S2C6 mAb (Francisco, J. A. et al. Cancer Res. 2000, 60, 3225-3231) or other anti-CD40 antibodies such as those disclosed in U.S. Patent Application Publication Nos. 2003/0211100 and 2002/0142358, mAb to the CD70 antigen, for example, 1F6 mAb and 2F2 mAb, and mAb to the CD30 antigen, for example, AC10 (Bowen, M. A. et al. J. Immunol. 1993, 151, 5896-5906, Wahl, A. F. et al. Cancer Res. 2002, 62(13), 3736-3742) or MDX-0060 (U.S. Patent Application Publication No. 2004/0006215).

The drug which can be used in the invention includes a chemotherapeutic agent. The chemotherapeutic agent is a compound useful in the treatment of cancer. Examples of the chemotherapeutic agent include the followings: alkylating agents, for example, thiotepa and cyclophosphamide (CY-TOXAN (trademark)); alkyl sulfonates, for example, busulfan, improsulfan and piposulfan; aziridines, for example, benzodopa, carboquone, meturedopa and uredopa; ethyleneimines and methylamelamines including altretamine, triethylenemelamine, triethylenephosphoramide, triethylenethiophosphoramide and trimethylolomelamine; acetogenins (particularly bullatacin and bullatacinone); camptothecin (including synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including synthetic analogs KW-2189 and CBI-TMI); eleutherobin; pancratistatin; sarcodictyin; spongistatin; nitrogen mustards, for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide and uracil mustard; nitrosoureas, for example, carmustine, chlorozotocin, fotemustine, lomustine, nimustine and ranimustine; antibiotics, for example, enediyne antibiotics (for example, calicheamicin), particularly calicheamicin gamma 1 and calicheamicin theta I, see, for example, Angew Chem Intl. Ed. Engl. 33:183-186 (1994); dynemicin, including dynemicin A; esperamicin; and neocarzinostatin chromophore and related chromoprotein enediyne antibiotic chromophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, for example, methotrexate and 5-fluorouracil (5-FU); folic acid analogs, for example, denopterin, methotrexate, pteropterin and trimetrexate; purine analogs, for example, fludarabine, 6-mercaptopurine, thiamiprine and thioguanine; pyrimidine analogs, for example, ancitabine, azacitidine, 6-azauridine, carmofur, cytarabine, dideoxyuridine, doxifluridine, enocitabine, floxuridine and 5-FU; androgens, for example, calusterone, dromostanolone propionate, epitiostanol, mepitiostane and testolactone; anti-adrenals, for example, aminoglutethimide, mitotane and trilostane; folic acid replenisher, for example, frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilone; etogiucid; gallium nitrate; hydroxy urea; lentinan; lonidamine; maytansinoids, for example, maytansine and ansamitocins; mitoguazone; mitoxantrone; mopidamol; nitracrine; pentostatin; phenamet; pirarubicin; podophyllinic acid; 2-ethylhydrazide; procarbazine; PSK (registered trademark); razoxane; rhizoxin; sizofiran: spirogermanium; tenuazonic acid; triaziquone; 2,2',2"-trichlorotriethylamine; trichothecenes (particularly T-2 toxin, verracurin A, roridin A and anguidine); urethane; vindesine; dacarbazine; mannomustine; mitobronitol; mitolactol; pipobroman; gacytosine; arabinoside ("Ara-C"); cyclophosphamide; thiotepa: taxoids, for example, paclitaxel (TAXOL (registered trademark), Bristol-Myers Squibb Oncology) and doxetaxel (TAXOTERE (registered trademark), Rhone-Poulenc Rorer); chlorambucil; gemcitabine; 6-thioguanine; mercaptopurine; methotrexate; platinum analogs, for example, cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of those described above. Anti-hormonal agents which act to regulate or inhibit hormone action on tumors, for example, anti-estrogen drugs including, for example, tamoxifen, raloxifene, 4(5)-imidazoles inhibiting aromatase, 4-hydroxytamoxifen, trioxifene, keoxifene, LY 117018, onapristone and toremifene (Fareston); and anti-androgen drugs, for example, the following are also included in the definition: for example, flutamide, nilutamide, bicalutamide, leuprolide and goserelin; siRNA, and pharmaceutically acceptable salts, acids or derivatives of any of those described above. Other chemotherapeutic agents which can be used with the invention are disclosed in U.S. Patent Application Publication Nos. 2008/0171040 and 2008/0305044, all of which are incorporated by reference in their entirety herein.

In a preferred embodiment of the invention, the chemotherapeutic agent is a low-molecular drug. The low-molecular drug has a molecular weight of preferably from 100 to 1,500, more preferably from 120 to 1,200, and still more preferably from 200 to 1,000. Typically, the low-molecular drug refers to an organic, inorganic or organometallic compound having a molecular weight of less than about 1,000, and the compounds are widely used. The low-molecular drugs of the invention also include oligopeptides and other biomolecules each having a molecular weight of less than about 1,000. The low-molecular drugs are well characterized in the art, for example, especially in WO 05/058367, EP-A-85901495, EP-A-8590319 and U.S. Pat. No. 4,956,303, and they are incorporated by reference in their entirety herein.

A preferred low-molecular drug of the invention is a low-molecular drug capable of being linked to the antibody. The invention includes known drugs as well as those which may become known. Particularly preferred low-molecular drugs include cytotoxic agents.

Preferred cytotoxic agents include maytansinoids, CC-1065 analogues, morpholinos, doxorubicins, taxanes, cryptophycins, epothilones, calicheamicins, auristatins and pyrrolobenzodiazepine dimers.

The antibody-drug conjugate containing the heterobifunctional monodispersed polyethylene glycol represented by the formula (2) of the invention can be prepared by bonding an antibody and a drug by using the heterobifunctional monodispersed polyethylene glycol represented by the formula (1). The preparation method of the antibody-drug conjugate represented by the formula (2) may be either a method in which the heterobifunctional monodispersed polyethylene glycol represented by the formula (1) is bonded to a drug and then bonded to an antibody or a method in which the heterobifunctional monodispersed polyethylene glycol represented by the formula (1) is bonded to an antibody and then bonded to a drug. Further, purification may be performed after either one of the antibody and the drug is bonded or may be performed after both the antibody and the drug are bonded.

A compound in which the heterobifunctional monodispersed polyethylene glycol represented by the formula (1) is bonded to the drug can be purified by a purification means, for example, column chromatography, extraction, recrystallization, adsorbent treatment, reprecipitation or supercritical extraction. Further, a compound in which the heterobifunctional monodispersed polyethylene glycol represented by the formula (1) is bonded to the antibody and an antibody-drug conjugate in which the heterobifunctional monodispersed polyethylene glycol represented by the formula (1) is bonded to both the antibody and the drug can be purified by a purification means, for example, column chromatography, extraction or adsorbent treatment.

The number of the drugs bonded to the antibody through the heterobifunctional monodispersed polyethylene glycol represented by the formula (1) of the invention is defined by an average number of drugs per antibody. The number of the drugs is preferably from 1 to 20, more preferably from 2 to 16, still more preferably from 3 to 12, and particularly preferably from 4 to 8.

The number of drugs per antibody in ADC can be determined by a method known to those skilled in the art, for example, ultraviolet/visible spectroscopy, mass spectrometry, ELISA method, electrophoresis, HPLC (High Performance Liquid Chromatography) or a combination of these methods.

$A^1$ in the formula (2) of the invention is a divalent spacer between a quaternary carbon atom of the branched portion and the monodispersed polyethylene glycol bonded to $X^2$, $B^2$ in the formula (2) is a divalent spacer between the quaternary carbon atom of the branched portion and $Y^2$, and $C^2$ in the formula (2) is a divalent spacer between the monodispersed polyethylene glycol bonded to $A^1$ and $X^2$, and these are composed of a covalent bond, respectively.

Specifically, A represents -$L^1$-$(CH_2)_{m1}$— or -$L^1$-$(CH_2)_{m1}$-$L^2$-$(CH_2)_{m2}$—, $L^1$ represents an ether bond, an amide bond, an urethane bond, a secondary amino group or a single bond, $L^2$ represents an amide bond or an urethane bond, and m1 and m2 represent each independently an integer of 1 to 5.

Further, $B^2$ represents -$L^3$-$(CH_2)_{m3}$-$L^6$-, -$L^3$-$(CH_2)_{m3}$-$L^4$-$(CH_2)_{m4}$-$L^6$- or -$L^6$-, $L^3$ represents an amide bond or a single bond, $L^4$ represents an ether bond, an amide bond or an urethane bond, and m3 and m4 represent each independently an integer of 1 to 5. Here, $L^6$ is an atomic group formed upon a reaction between the functional group contained in $Y^1$ of the heterobifunctional monodispersed polyethylene glycol represented by the formula (1) and a functional group present in the antibody or the drug, and is preferably an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group or a hydrocarbon group containing any of them.

Moreover, $C^2$ represents -$L^5$-$(CH_2)_{m5}$-L-, —O—$CH_2$-$L^7$- or -$L^7$-, $L^5$ represents an amide bond, an urethane bond, a secondary amino group or a single bond, and m5 represents an integer of 1 to 5. Here, $L^7$ is an atomic group formed upon a reaction between the functional group contained in $X^1$ of the heterobifunctional monodispersed polyethylene glycol represented by the formula (1) and a functional group present in the antibody or the drug, and is preferably an amide bond, an urethane bond, a thioether bond, a disulfide bond, a carbonate bond, an ester bond, an ether bond, a 1H-1,2,3-triazole-1,4-diyl structure, a secondary amino group, a hydrazide group, an oxyamide group or a hydrocarbon group containing any of them.

EXAMPLES

The present invention will be described more specifically with reference to Examples, but the invention should not be construed as being limited thereto.

In $^1$H-NMR analysis, "JNM-ECP400" or "JNM-ECA600" manufactured by JEOL DATUM Ltd. was used. For the measurement, a tube of 5 mm φ was used, and tetramethylsilane (TMS) was used as an internal standard substance in the case where a deuterated solvent was $CDCl_3$, $CD_2Cl_2$, or $CD_3OD$.

Example 1

Into a 500 mL four-necked flask equipped with a thermometer, a nitrogen inlet tube, a stirrer, a Dean-stark tube and a condenser tube were charged trishydroxymethylaminomethane (30.3 g, 250 mmol), sodium carbonate (5.30 g, 50 mmol), dehydrated methanol (237 g) and benzonitrile (5.15 g, 50 mmol), and the reaction was performed at 65° C. for 24 hours. After the reaction mixture was filtered and the solvent was distilled off under a reduced pressure, the residue was dissolved by adding isopropyl alcohol and dichloromethane, and the solution was washed with an aqueous 10% by weight sodium chloride solution. The organic layer was dried over anhydrous sodium sulfate, filtered, and the solvent was distilled off under a reduced pressure. The residue was dissolved in THF (tetrahydrofuran), and crystallization was performed by adding hexane, followed by filtration to obtain a compound of the formula (24).

$^1$H-NMR ($CDCl_3$, internal standard TMS); δ (ppm):
3.06 (2H, brs, —OH),
3.65-3.81 (4H, dd, >C(CH$_2$OH)$_2$),
4.38 (2H, s, —CNO—C$\underline{H}$—),
7.32-7.83 (5H, m, arom. $\underline{H}$)

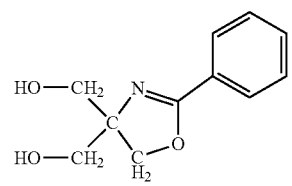

(24)

Example 2

Into a 100 mL three-necked flask equipped with a thermometer, a nitrogen inlet tube, a stirring bar, a Dean-stark tube and a condenser tube were charged dodecaethylene glycol monomethyl ether (10.4 g, 18.5 mmol), toluene (52.0 g), triethylamine (2.44 g, 24.1 mmol) and methanesulfonyl chloride (2.34 g, 20.4 mmol), and the reaction was performed at 40° C. for 3 hours. The reaction solution was diluted by adding dichloromethane and then washed with water, and the organic layer was dried over anhydrous magnesium sulfate. After filtration, the solvent was distilled off under a reduced pressure to obtain a compound of the formula (25).

$^1$H-NMR (CDCl$_3$, internal standard TMS); δ (ppm):

3.08 (3H, s, —O—SO$_2$—C$\underline{H}_3$), 3.38 (3H, s, —O—C$\underline{H}_3$), 3.45-3.85 (46H, m, CH$_3$—O—(C$\underline{H}_2$C$\underline{H}_2$O)$_{11}$—C$\underline{H}_2$CH$_2$—O—SO$_2$—CH$_3$), 4.38 (2H, m, —C$\underline{H}_2$—O—SO$_2$—CH$_3$)

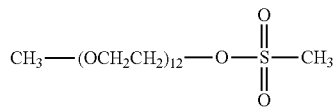
(25)

Example 3

Into a 50 mL three-necked flask equipped with a thermometer, a nitrogen inlet tube, a stirring bar, a Dean-stark tube and a condenser tube were charged the compound of the formula (24) (0.21 g, 1.01 mmol), dehydrated THF (7.70 g), the compound of the formula (25) (2.46 g, 3.84 mmol), 1M tert-butoxy potassium THF solution (3.72 g. 4.04 mmol), and the reaction was performed at 50° C. for 4 hours. After adding dichloromethane and an aqueous 25% by weight sodium chloride solution, water washing was performed, and the organic layer was dried over anhydrous sodium sulfate. After filtration, the solvent was distilled off under a reduced pressure to obtain a compound of the formula (26).

$^1$H-NMR (CDCl$_3$, internal standard TMS); δ (ppm):

3.38 (6H, s, —O—C$\underline{H}_3$), 3.40-3.75 (100H, m, >C(C$\underline{H}_2$O)$_2$—, —O—(C$\underline{H}_2$C$\underline{H}_2$O)$_{12}$—), 4.36 (2H, s, —CNO—C$\underline{H}_2$—), 7.37-7.94 (5H, m, arom. H)

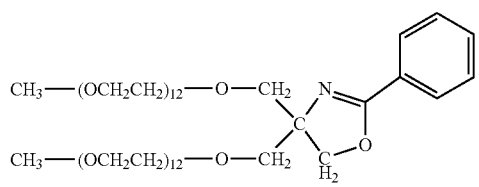
(26)

Example 4

To a 100 mL three-necked flask equipped with a thermometer, a nitrogen inlet tube, a stirring bar, a Dean-stark tube and a condenser tube were added the compound of the formula (26) (1.13 g, 0.877 mmol) and distilled water (31.1 g), and the compound was dissolved. After adding 85% phosphoric acid (0.43 mL) to adjust pH to 1.5, the reaction was performed at 50° C. for 3 hours. Then, after adding an aqueous 400 g/L sodium hydroxide solution (5.58 mL) with cooling, the reaction was performed at 50° C. for 6 hours. Subsequently, 6N hydrochloric acid was added to adjust pH to 2.0 and then toluene and chloroform were added thereto to perform washing. Sodium chloride was added so as to be an aqueous 25% sodium chloride solution and then, using an aqueous 400 g/L sodium hydroxide solution, pH was adjusted to 12.5. Extraction was performed by using toluene, and the extract was dried over anhydrous sodium sulfate. After filtration, the solvent was distilled off under a reduced pressure to obtain a compound of the formula (27).

$^1$H-NMR (CDCl$_3$, internal standard TMS); δ (ppm):

3.08 (1H, brs, —O$\underline{H}$), 3.38 (6H, s, —O—C$\underline{H}_3$), 3.40-3.80 (102H, m, >C(C$\underline{H}_2$O)$_2$—, —O—(C$\underline{H}_2$CH$_2$-O)$_{12}$—, >CNH$_2$—C$\underline{H}_2$—OH)

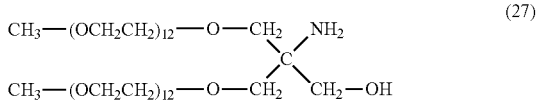
(27)

Example 5

Into a 50 mL three-necked flask equipped with a thermometer, a nitrogen inlet tube, a stirring bar, a Dean-stark tube and a condenser tube were charged the compound of the formula (27) (1.50 g, 1.24 mmol), 31-(2,5-dihydro-2,5-dioxo-1H-pyrrol-1-yl)-29-oxo-4,7,10,13,16,19,22,25-octaoxa-28-azahentriacontanoic acid (0.811 g, 1.37 mmol), DMT-MM (0.377 g, 1.37 mmol), acetonitrile (15.0 g) and triethylamine (0.151 g, 1.49 mmol), and the reaction was performed at 25° C. for 9 hours. A citrate buffer of pH 3.0 (18.0 g) was added thereto and then washing was performed by using toluene. Extraction was performed by using toluene and chloroform, and then the organic layer was washed by using a citrate buffer of pH 3.0 and a phosphate buffer of pH 7.0. Further, the organic layer was washed with an aqueous 20% sodium chloride solution and then dried over anhydrous magnesium sulfate. After filtration, the solvent was distilled off under a reduced pressure to obtain a compound of the formula (28). Incidentally, DMT-MM means 4-(4,6-dimethoxy-1,3,5-triazin-2-yl)-4-methylmorpholinium chloride.

$^1$H—NMR (CD$_2$Cl$_2$, internal standard TMS); δ (ppm):
2.46 (4H, m, —O—CH$_2$C$\underline{H}_2$—CONH—, —C$\underline{H}_2$CH$_2$-maleimide),
3.38 (6H, s, —O—C$\underline{H}_3$),
3.45-3.79 (138H, m, >C(C$\underline{H}_2$O)$_2$—, —O—(C$\underline{H}_2$C$\underline{H}_2$-O)$_{12}$—, —CONH—(C$\underline{H}_2$C$\underline{H}_2$O)$_8$—C$\underline{H}_2$CH$_2$—CONH—, >CNH—C$\underline{H}_2$—OH, —C$\underline{H}_2$-maleimide),
4.65 (1H, t, —O$\underline{H}$),
6.42 (1H, s, —O—CH$_2$CH$_2$—CON$\underline{H}$—),
6.69 (2H, s, -maleimide),
6.72 (1$\underline{H}$, s, —NH—CO—CH$_2$CH$_2$-maleimide)

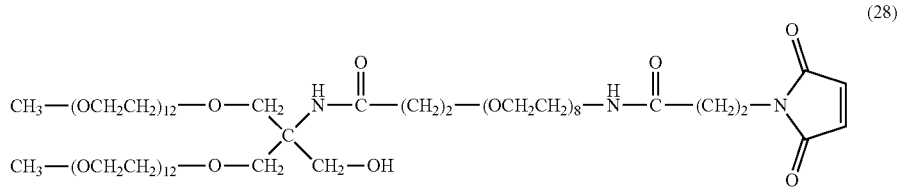

(28)

Example 6

To a 50 mL three-necked flask equipped with a thermometer, a nitrogen inlet tube, a stirring bar, a Dean-stark tube and a condenser tube were added the compound of the formula (28) (0.700 g, 0.393 mmol), N-phenylmorpholine (0.160 g, 0.983 mmol), p-nitorophenyl chloroformate (0.158 g, 0.786 mmol) and dichloromethane (5.22 g), and the reaction was performed at 25° C. for 3 hours. Distilled water (0.042 g, 2.36 mmol) and N-phenylmorpholine (0.160 g, 0.983 mmol) were added thereto, the mixture was stirred at 25° C. for 2 hours and then diluted with hexane. The mixture was washed by using 0.2M hydrochloric acid and then washed by using a borate buffer of pH 10.0 and an aqueous 10% sodium chloride solution. The organic layer was dried over anhydrous sodium sulfate, filtered, and then the solvent was distilled off under a reduced pressure. The residue was dissolved in acetonitrile, the resulting solution was washed by adding hexane and tert-butanol, and the solvent was distilled off under a reduced pressure to obtain a compound of the formula (29).

$^1$H-NMR (CDCl$_3$, internal standard TMS); δ (ppm):
2.44 (2H, t, —O—C$\underline{H}_2$CH—CONH—),
2.51 (2H, t, —CONH—C$\underline{H}_2$CH$_2$-maleimide),
3.38 (6H, s, —O—C$\underline{H}_3$),
3.42 (2H, m, —C$\underline{H}_2$—CONH—CH$_2$CH$_2$-maleimide),
3.45-3.90 (134H, m, >C(C$\underline{H}_2$O)$_2$—, —O—(C$\underline{H}_2$C$\underline{H}_2$-O)$_{12}$—, —CONH—C$\underline{H}_2$CHO—(C$\underline{H}_2$C$\underline{H}_2$O)$_7$—CH$_2$CH$_2$—CONH—, —C$\underline{H}_2$-maleimide),
4.70 (2H, s, >CNH—C$\underline{H}_2$—OCOO—),
6.42 (1H, s, —N$\underline{H}$—CO—CH$_2$CH$_2$-maleimide),
6.53 (1H, s, —O—CH$_2$CH$_2$—CON$\underline{H}$—)
6.70 (2H, s, -maleimide),
7.39-8.29 (4H, m, arom. H)

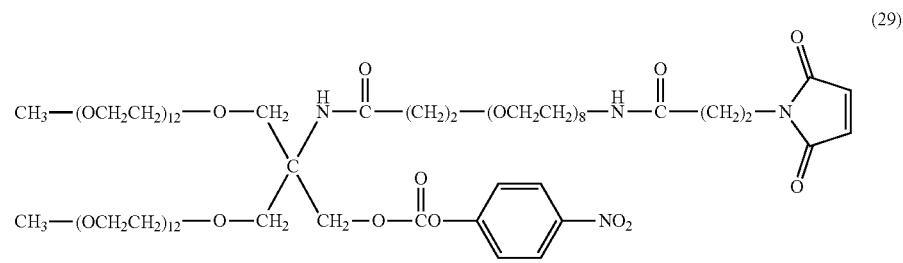

(29)

Example 7

To a 4-mL screw tube containing a stirring bar were charged doxorubicin hydrochloride (6.8 mg, 11.7 µmol), N,N-diisopropylamnine (4.55 mg, 35.0 µmol)), N,N-dimethylformamide and the compound of the formula (29) (20.6 mg, 10.6 µmol), and the reaction was performed for 4 hours. After dilution with dichloromethane, the mixture was washed by using an aqueous 5% by weight sodium dihydrogen phosphate 12-hydrate solution and then using ion exchange water. The organic layer was dried over anhydrous sodium sulfate, filtered, and the solvent was distilled off under a reduced pressure to obtain a drug-linker compound of the formula (30).

$^1$H-NMR (CDCl$_3$, internal standard TMS); δ (ppm): 1.30 (3H, m), 1.85-2.18 (2H, s), 2.38-2.41 (2H, m), 2.52 (2H, t), 3.04 (1H, s), 3.38 (6H, s), 3.40-3.44 (2H, m), 3.45-3.90 (139H, m), 4.09 (3H, s), 4.32 (2H, dd), 4.69 (1H, s), 4.78 (2H, d), 5.33 (1H, s), 5.53 (1H, s), 5.71 (1H, d), 6.54 (1H, s), 6.59 (1H, t), 6.71 (2H, s), 7.41 (1H, d), 7.80 (1H, t), 8.06 (1H, d)

Gradient program: 0% to 0% (0 minute to 2.5 minutes), 0% to 100% (2.5 minutes to 35 minutes), 100% to 0% (35.1 minutes to 45 minutes)

Example 9

Monoclonal anti-interleukin-1 beta antibody produced in mouse (0.500 mg, Sigma-Aldrich) was dissolved in phosphate buffered saline (PBS, 0.500 mL). The solution (0.048 mL) was put into a 0.5 mL polyethylene tube, 50.0 mM of ethylenediamine tetraacetic acid (EDTA, 0.006 mL) and an aqueous 0.800 mM tris(2-carboxymethyl)phosphine hydrochloride (TCEP) solution (0.006 mL; 15 equivalents to the antibody) were added thereto, and the mixture was shaken at 37° C. for one hour. To the solution was added a solution containing N,N-dimethylacetamide and 2.50 mM of the compound of the formula (30) (0.007 mL; 53 equivalents to the antibody), and the mixture was further shaken at 20° C. for one hour. An aqueous 2.50 mM N-acetylcysteine (0.007 mL; 53 equivalents to the antibody) solution was added thereto, and the resulting mixture was further shaken at 20°

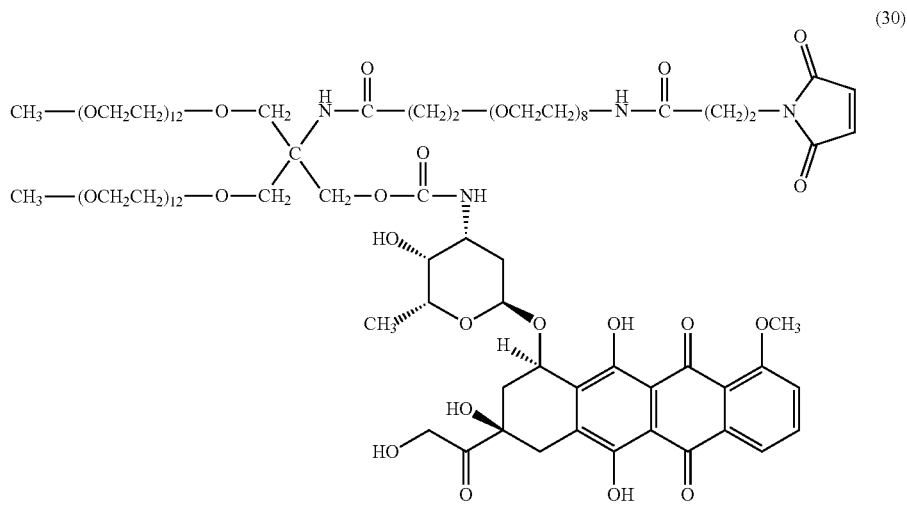

(30)

Example 8

As to the drug-linker compound of the formula (30) obtained in Example 7, HPLC measurement was performed using a hydrophobic interaction chromatography (HIC) column under the measurement conditions described below. A chart of the results at a measurement wavelength of 495 nm was shown in FIG. 1.

HPLC apparatus: Alliance (Waters)
Column: TSKgel Butyl-NPR (4.6×35 mm, 2.5 m; Tosoh Corp.)
Flow rate: 0.8 mL/minute,
Analysis time: 45 minutes,
Column temperature: 25° C.,
Injection amount: 100 µL,
Detector: UV-visible spectrophotometer (measurement wavelength: 280 nm and 495 nm)
Mobile phase A: 50 mM sodium phosphate buffer solution (pH 7.0) containing 1.5 M ammonium sulfate
Mobile phase B: mixed solution containing 80% of 50 mM sodium phosphate buffer solution (pH 7.0) and 20% of isopropyl alcohol C. for one hour. The resulting solution was filled in a NAP-5 column (GE Healthcare Life Science) equilibrated by using PBS (10 mL) and eluted with PBS to separate an antibody fraction.

Example 10

An average binding number per antibody in an antibody-drug conjugate can be calculated by measuring the UV absorbance of an aqueous solution of the antibody-drug conjugate at two wavelengths of 280 nm and 495 nm and then performing the calculation shown below.

Since the total absorbance at a certain wavelength is equal to the sum of the absorbance of all the absorbing chemical species present in the system (additivity of absorbance), assuming that there is no change in the molar extinction coefficient of the antibody and the drug before and after the conjugation reaction between the antibody and the drug, the antibody concentration and the drug concentration in the antibody-drug conjugate are represented by the relational expression shown below.

$$A_{280}=A_{D,280}+A_{A,280}=\varepsilon_{D,280}C_D+\varepsilon_{A,280}C_A \quad \text{Formula (i)}$$

$$A_{495}=A_{D,495}+A_{A,495}=\varepsilon_{D,495}C_D+\varepsilon_{A,495}C_A \quad \text{Formula (ii)}$$

Here, $A_{280}$ indicates the absorbance of the aqueous solution of the antibody-drug conjugate at 280 nm, $A_{495}$ indicates the absorbance of the aqueous solution of the antibody-drug conjugate at 495 nm, $A_{A,280}$ indicates the absorbance of the antibody at 280 nm, $A_{A,495}$ indicates the absorbance of the antibody at 495 nm, $A_{D,280}$ indicates the absorbance of the drug-linker compound at 280 nm, $A_{D,495}$ indicates the absorbance of the drug-linker compound at 495 nm, $\varepsilon_{A,280}$ indicates the molar extinction coefficient of the antibody at 280 nm, $\varepsilon_{A,495}$ indicates the molar extinction coefficient of the antibody at 495 nm, $\varepsilon_{D,280}$ indicates the molar extinction coefficient of the drug-linker compound at 280 nm, $\varepsilon_{D,495}$ indicates the molar extinction coefficient of the drug-linker compound at 495 nm, $C_A$ indicates the antibody concentration in the antibody-drug conjugate, and $C_D$ indicates the drug concentration in the antibody-drug conjugate.

Here, for $\varepsilon_{A,280}$, $\varepsilon_{A,495}$, $\varepsilon_{D,280}$ and $\varepsilon_{D,495}$, values previously prepared (estimated values or measured values obtained from UV measurement of the compound) are used. $\varepsilon_{A,495}$ is ordinarily 0. $\varepsilon_{D,280}$ and $\varepsilon_{D,495}$ can be obtained by measuring the absorbance of a solution in which the drug-linker compound used is dissolved in a certain molar concentration and calculating each value according to Lambert-Beer law (absorbance=molar concentration×molar extinction coefficient×cell optical path length). $C_A$ and $C_D$ can be determined by measuring $A_{280}$ and $A_{495}$ of the aqueous solution of the antibody-drug conjugate and substituting these values into the formula (i) and the formula (ii) to solve the simultaneous equations. Further, the average drug binding number per antibody can be determined by dividing $C_D$ by $C_A$.

When the simultaneous equations described above was solved using molar extinction coefficients $\varepsilon_{A,280}$=206999 (estimated value), $\varepsilon_{A,495}$=0, $\varepsilon_{D,280}$=12786 (measured value) and $\varepsilon_{D,495}$=12558 (measured value), the average drug binding number per antibody was 7.6.

Comparative Example 1

Into a 100 mL three-necked flask equipped with a thermometer, a nitrogen inlet tube, a stirring bar, a Dean-stark tube and a condenser tube were charged 2-amino-2-methyl-1,3-propanediol (13.1 g, 125 mmol), sodium carbonate (2.65 g, 25 mmol), dehydrated methanol (19.8 g) and benzonitrile (2.58 g, 25 mmol), and the reaction and purification were performed in the same manner as in Example 1 to obtain a compound of the formula (31).

¹H-NMR (CD₃OD, internal standard TMS); δ (ppm):
1.33 (3H, s, >CC$\underline{H}_3$—CH₂—OH),
3.49-3.60 (2H, dd, >CCH₃—C$\underline{H}_2$—OH),
4.10-4.53 (2H, dd, —CNO—C$\underline{H}_2$—),
7.43-7.93 (5H, m, arom. H)

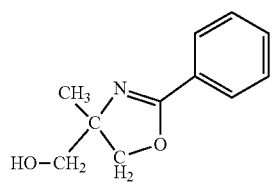

(31)

Comparative Example 2

Into a 50 mL three-necked flask equipped with a thermometer, a nitrogen inlet tube, a stirring bar, a Dean-stark tube and a condenser tube were charged the compound of the formula (31) (0.130 g, 0.680 mmol), dehydrated THF (1.87 g), the compound of the formula (25) (0.651 g, 1.02 mmol), and a 1M tert-butoxy potassium THF solution (0.928 g. 1.02 mmol), and the reaction and purification were performed in the same manner as in Example 3 to obtain a compound of the formula (32).

¹H-NMR (CDCl₃, internal standard TMS); δ (ppm):
1.37 (3H, s, >CC$\underline{H}_3$—CH₂—O—CH₂—),
3.38 (3H, s, —O—C$\underline{H}_3$),
3.40-3.80 (50H, m, >CCH₃—CH₂—O—C$\underline{H}_2$—, —O—(C$\underline{H}_2$C$\underline{H}_2$O)₁₂—),
4.01-4.47 (2H, dd, —CNO—C$\underline{H}_2$—),
7.38-7.95 (5H, m, arom. H)

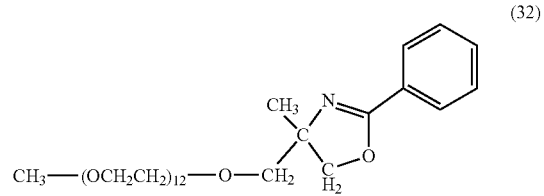

(32)

Comparative Example 3

To a 50 mL three-necked flask equipped with a thermometer, a nitrogen inlet tube, a stirring bar, a Dean-stark tube and a condenser tube were added the compound of the formula (32) (0.160 g, 0.218 mmol) and distilled water (4.40 g), and the compound was dissolved. After adding 85% phosphoric acid (0.11 mL) to adjust pH to 1.5, the reaction was performed at 50° C. for 6 hours. After adding an aqueous 400 g/L sodium hydroxide solution (1.40 mL) with cooling, the reaction was performed at 50° C. for 5 hours. Subsequently, 6N hydrochloric acid was added to adjust pH to 2.0 and then toluene and chloroform were added thereto to perform washing. Thereafter, purification was performed in the same manner as in Example 4 to obtain a compound of the formula (33).

¹H-NMR (CDCl₃, internal standard TMS); δ (ppm):
1.03 (3H, s, >CC$\underline{H}_3$—CH₂—O—),
2.91 (1H, brs, —O$\underline{H}$),
3.38 (3H, s, —O—C$\underline{H}_3$),
3.00-3.85 (52H, m, >CCH₃—C$\underline{H}_2$—O—CH₂—, —O—(C$\underline{H}_2$C$\underline{H}_2$O)₁₂—, >CCH₃—C$\underline{H}_2$—OH)

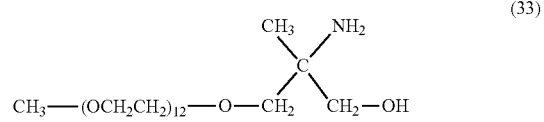

(33)

Comparative Example 4

Into a 4-mL screw tube containing a stirring bar were charged the compound of the formula (33) (0.0920 g, 0.142 mmol), 6-maleimidohexanoic acid (0.0345 g, 0.163 mmol), DMT-MM (0.0564 g, 0.163 mmol), acetonitrile (0.980 g) and triethylamine (0.0172 g, 0.170 mmol), and the reaction was performed at 25° C. for 5 hours. A citrate buffer of pH 3.0 (1.10 g) was added thereto and then washing was performed by using toluene. Thereafter, purification was performed in the same manner as in Example 5 to obtain a compound of the formula (34).
¹H-NMR (CDCl₃, internal standard TMS); δ (ppm):
1.27 (3H, s, >CCH₃—CH₂—O—),
1.32 (2H, m, —CH₂CH₂CH₂—CONH—),
1.63 (4H, m, —CH₂CH₂CH₂CH₂—CONH—),
2.18 (2H, t, —CH₂—CONH—),
3.38 (3H, s, —O—CH₃),
3.40-3.80 (54H, m, >CCH₃—CH₂—O—CH₂—, —O—(CH₂CH₂O)₁₂—, >CCH₃—CH₂—OH, —CH₂-maleimide)
4.62 (1H, brs, —OH),
6.20 (1H, s, —CH₂—CONH—),
6.69 (2H, s, -maleimide)

¹H-NMR (CDCl₃, internal standard TMS); δ (ppm):
1.32 (2H, m, —CH₂CH₂CH₂—CONH—),
1.45 (3H, s, >CCH₃—CH₂—O—),
1.60 (4H, m, —CH₂CH₂CH₂CH₂—CONH—),
2.15 (2H, t, —CH₂—CONH—),
3.38 (3H, s, —O—CH₃),
3.41-3.80 (52H, m, >CCH₃—CH₂—O—CH₂—, —O—(CH₂CH₂O)₁₂—, —CH₂-maleimide),
4.51-4.59 (2H, dd, >CCH₃—CH₂—OCOO—),
5.92 (1H, s, —CH₂—CONH—),
6.68 (2H, s, -maleimide),
7.39-8.29 (4H, m, arom. H)

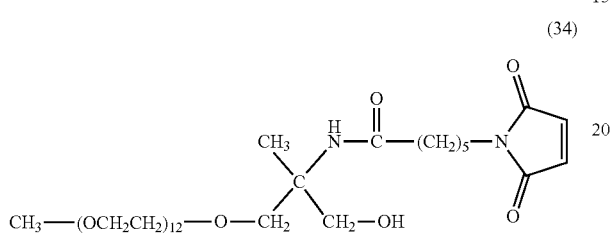

(34)

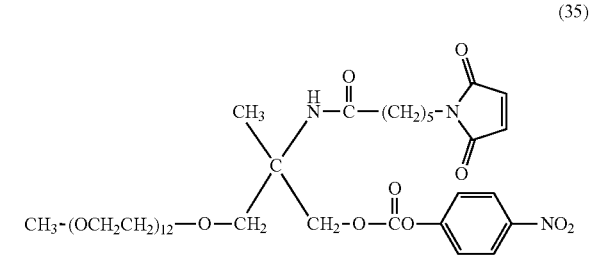

(35)

Comparative Example 5

To a 4 ml screw tube containing a stirring bar were added the compound of the formula (34) (0.050 g, 0.0595 mmol), N-methylmorpholine (0.0601 g, 0.595 mmol), (4-bisnitrophenyl) carbonate (0.145 g, 0.476 mmol) and dehydrated acetonitrile (0.467 g), and the reaction was performed at 25° C. for 4 hours in a nitrogen atmosphere. Distilled water (0.030 g, 1.67 mmol) and N-methylmorpholine (0.0361 g, 0.357 mmol) were added, and the mixture was stirred at 25° C. for 6 hours and then diluted with dichloromethane. The diluted one was washed by using a citrate buffer of pH 3.0, and then further washed by using a borate buffer of pH 10.0 and a 25% saline. The organic layer was dried over anhydrous sodium sulfate, filtered, and then the solvent was distilled off under reduced pressure to give the compound of the formula (35).

Comparative Example 6

Into a 4-mL screw tube containing a stirring bar were charged doxorubicin hydrochloride (6.34 mg, 10.9 μmol), N,N-diisopropylamine (2.95 mg, 22.9 μmol), N,N-dimethylformamide and the compound of the formula (35) (10.0 mg, 9.94 μmol), and the reaction was performed for 4 hours. Thereafter, purification was performed in the same manner as in Example 7 to obtain a drug-linker compound of the formula (36).
¹H-NMR (CDCl₃, internal standard TMS); δ (ppm):
1.25-1.34 (8H, m), 1.55-1.65 (4H, m), 1.75-1.88 (2H, m), 2.06-2.10 (2H, m), 2.16-2.38 (2H, m), 2.88 (1H, dd), 3.00 (1H, s), 3.18 (2H, dd) 3.38 (3H, s), 3.41-3.90 (60H, m), 4.03-4.06 (1H, m), 4.09 (3H, s), 4.12-4.14 (1H, m), 4.61 (1H, s), 4.77 (2H, d), 5.32 (1H, s), 5.43-5.48 (1H, m), 5.53 (1H, s), 6.06 (1H, d), 6.68 (2H, s), 7.41 (1H, d), 7.80 (1H, t), 8.06 (1H, d)

(36)

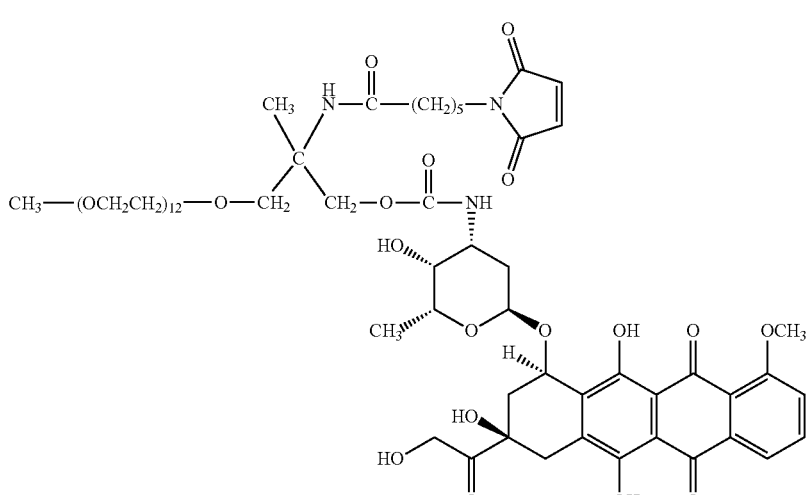

Comparative Example 7

As to the drug-linker compound of the formula (36) obtained in Comparative Example 6, HPLC measurement was performed using a hydrophobic interaction chromatography (HIC) column under the same measurement conditions as in Example 8. A chart of the results at a measurement wavelength of 495 nm was shown in FIG. 2

Comparative Example 8

Into a 50 mL three-necked flask equipped with a thermometer, a nitrogen inlet tube, a stirring bar, a Dean-stark tube and a condenser tube were charged tetracosaethylene glycol monomethyl ether (2.05 g, 1.88 mmol), toluene (10.3 g), triethylamine (0.552 g, 5.45 mmol) and methanesulfonyl chloride (0.478 g, 4.17 mmol), and the reaction was performed at 25° C. for 8 hours. The reaction solution was diluted by adding dichloromethane and then washed with water, and the organic layer was dried over anhydrous magnesium sulfate. After filtration, the solvent was distilled off under a reduced pressure to obtain a compound of the formula (37).

$^1$H-NMR (CDCl$_3$, internal standard TMS); δ (ppm):
3.09 (3H, s, —O—SO$_2$—C$\underline{H}_3$),
3.38 (3H, s, —OC$\underline{H}_3$),
3.45-3.85 (94H, m, CH$_3$—O—(CH$_2$C$\underline{H}_2$O)$_{23}$—C$\underline{H}_2$CH$_2$—O—SO$_2$—CH$_3$),
4.38 (2H, m, —C$\underline{H}_2$—O—SO$_2$—CH$_3$)

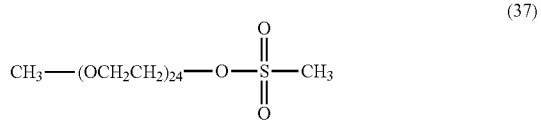
(37)

Comparative Example 9

Into a 50 mL three-necked flask equipped with a thermometer, a nitrogen inlet tube, a stirring bar, a Dean-stark tube and a condenser tube were charged the compound of the formula (31) (0.174 g, 0.910 mmol), dehydrated THF (2.86 g), the compound of the formula (37) (1.38 g, 1.18 mmol), a 1M tert-butoxy potassium THF solution (1.82 g. 2.00 mmol), and the reaction and purification were performed in the same manner as in Example 3 to obtain a compound of the formula (38).

$^1$H-NMR (CDCl$_3$, internal standard TMS); δ (ppm):
1.37 (3H, s, >CC$\underline{H}_3$—CH$_2$—O—CH$_2$—),
3.38 (3H, s, —O—C$\underline{H}_3$),
3.40-3.80 (98H, m, >CCH$_3$—C$\underline{H}_2$—O—CH$_2$—, —O—(C$\underline{H}_2$C$\underline{H}_2$O)$_{24}$—),
4.01-4.47 (2H, dd, —CNO—C$\underline{H}_2$—),
7.38-7.95 (5H, m, arom. $\underline{H}$)

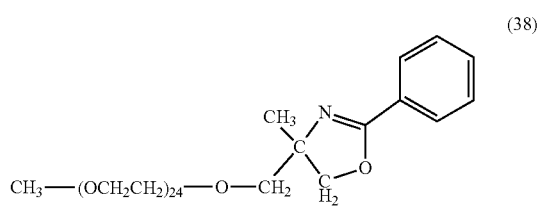
(38)

Comparative Example 10

To a 50 mL three-necked flask equipped with a thermometer, a nitrogen inlet tube, a stirring bar, a Dean-stark tube and a condenser tube were added the compound of the formula (38) (0.909 g, 0.720 mmol) and distilled water (25.0 g), and the compound was dissolved. After adding 85% phosphoric acid (0.250 mL) to adjust pH to 1.5, the reaction was performed at 50° C. for 6 hours. After adding an aqueous 400 g/L sodium hydroxide solution (7.63 mL) with cooling, the reaction was performed at 50° C. for 10 hours. Subsequently, 6N hydrochloric acid was added to adjust pH to 2.0 and then toluene and chloroform were added thereto to perform washing. Thereafter, purification was performed in the same manner as in Example 4 to obtain a compound of the formula (39).

$^1$H-NMR (CDCl$_3$, internal standard TMS); δ (ppm):
1.03 (3H, s, >CC$\underline{H}_3$—CH$_2$—O—),
3.00 (1H, brs, —O$\underline{H}$),
3.38 (3H, s, —O—C$\underline{H}_3$),
3.30-3.85 (100H, m, >CCH$_3$—C$\underline{H}_2$—O—CH$_2$—, —O—(C$\underline{H}_2$C$\underline{H}_2$O)$_4$—, >CCH$_3$—C$\underline{H}_2$—OH)

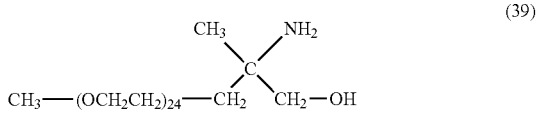
(39)

Comparative Example 11

Into a 50 mL three-necked flask equipped with a thermometer, a nitrogen inlet tube, a stirring bar, a Dean-stark tube and a condenser tube were charged the compound of the formula (39) (0.729 g, 0.620 mmol), 6-maleimidohexanoic acid (0.164 g, 0.775 mmol), DMT-MM (0.214 g, 0.775 mmol), acetonitrile (7.29 g) and triethylamine (0.082 g, 0.806 mmol), and the reaction was performed at 25° C. for 3 hours. A citrate buffer of pH 3.0 (8.75 g) was added thereto and then washing was performed by using toluene. Thereafter, purification was performed in the same manner as in Example 5 to obtain a compound of the formula (40).

$^1$H-NMR (CDCl$_3$, internal standard TMS); δ (ppm):
1.23 (3H, s, >CC$\underline{H}_3$—CH$_2$—O—),
1.32 (2H, m, —C$\underline{H}_2$CH$_2$CH$_2$—CONH—),
1.63 (4H, m, —C$\underline{H}_2$CH$_2$CH$_2$C$\underline{H}_2$—CONH—),
2.18 (2H, t, —C$\underline{H}_2$—CONH—),
3.38 (3H, s, —O—C$\underline{H}_3$),
3.40-3.80 (102H, m, >CCH$_3$—C$\underline{H}_2$—O—CH$_2$—, —O—(C$\underline{H}_2$C$\underline{H}_2$O)$_{24}$—, >CCH$_3$—C$\underline{H}_2$—OH, —C$\underline{H}_2$-maleimide),
4.71 (1H, brs, —O$\underline{H}$),
6.26 (1H, s, —CH$_2$—CON$\underline{H}$—),
6.69 (2H, s, -maleimide)

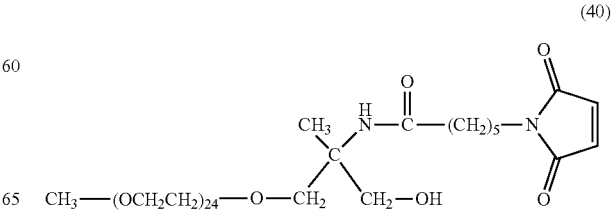
(40)

Comparative Example 12

To a 50 mL three-necked flask equipped with a thermometer, a nitrogen inlet tube, a stirring bar, a Dean-stark tube and a condenser tube were added the compound of the formula (40) (0.600 g, 0.438 mmol), N-phenylmorpholine (0.179 g, 1.10 mmol), p-nitrophenyl chloroformate (0.177 g, 0.876 mmol) and dichloromethane (5.81 g), and the reaction was performed at 25° C. for 3 hours. Distilled water (0.047 g, 2.63 mmol) and N-phenylmorpholine (0.179 g, 1.10 mmol) were added thereto, the mixture was stirred at 25° C. for 6 hours and then diluted with hexane. Thereafter, purification was performed in the same manner as in Example 6 to obtain a compound of the formula (41).

$^1$H-NMR (CDCl$_3$, internal standard TMS); δ (ppm):

N,N-diisopropylamine (2.51 mg, 19.4 μmol), N,N-dimethylformamide and the compound of the formula (35) (13.0 mg, 8.47 μmol), and the reaction was performed for 4 hours. Thereafter, purification was performed in the same manner as in Example 7 to obtain a drug-linker compound of the formula (42).

$^1$H-NMR (CDCl$_3$, internal standard TMS); δ (ppm):

1.25-1.34 (8H, m), 1.55-1.65 (4H, m), 1.75-1.88 (2H, m), 2.06-2.10 (2H, m), 2.16-2.38 (2H, m), 2.88 (1H, dd), 3.00 (1H, s), 3.18 (2H, dd), 3.38 (3H, s), 3.41-3.90 (103H, m), 4.03-4.06 (1H, m), 4.09 (3H, s), 4.12-4.14 (1H, m), 4.61 (1H, s), 4.77 (2H, d), 5.32 (1H, s), 5.43-5.48 (1H, m), 5.53 (1H, s), 6.06 (1H, d), 6.68 (2H, s), 7.41 (1H, d), 7.80 (1H, t), 8.06 (1H, d)

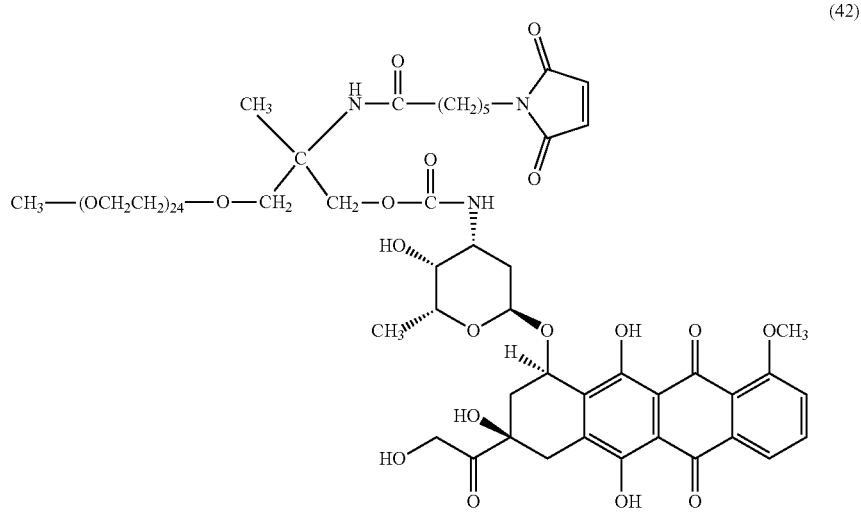

(42)

1.28 (2H, m, —C$\underline{H}_2$CH$_2$CH$_2$—CONH—),
1.41 (3H, s, >CC$\underline{H}_3$—CH$_2$—O—),
1.63 (4H, m, —C$\underline{H}_2$CH$_2$CH$_2$CH$_2$—CONH—),
2.15 (2H, t, —C$\underline{H}_2$—CONH—),
3.38 (3H, s, —O—C$\underline{H}_3$),
3.41-3.80 (100H, m, >CC$\underline{H}_3$—C$\underline{H}_2$—O—C$\underline{H}_2$—, —O—(C$\underline{H}_2$C$\underline{H}_2$O)$_{24}$—, —C$\underline{H}_2$-maleimide),
4.51-4.60 (2H, dd, >CC$\underline{H}_3$—C$\underline{H}_2$—OCOO—),
6.01 (1H, s, —CH$_2$—CON$\underline{H}$—),
6.69 (2H, s, -maleimide),
7.38-8.36 (4H, m, arom. $\underline{H}$)

(41)

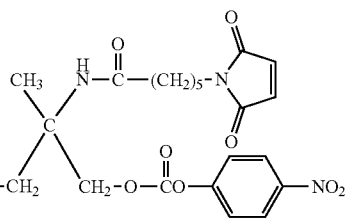

Comparative Example 13

Into a 4-mL screw tube containing a stirring bar were charged doxorubicin hydrochloride (5.40 mg, 9.31 μmol),

Comparative Example 14

As to the drug-linker compound of the formula (42) obtained in Comparative Example 13, HPLC measurement was performed using a hydrophobic interaction chromatography (HIC) column under the same measurement conditions as in Example 8. A chart of the results at a measurement wavelength of 495 nm was shown in FIG. 3.

Figure 2:
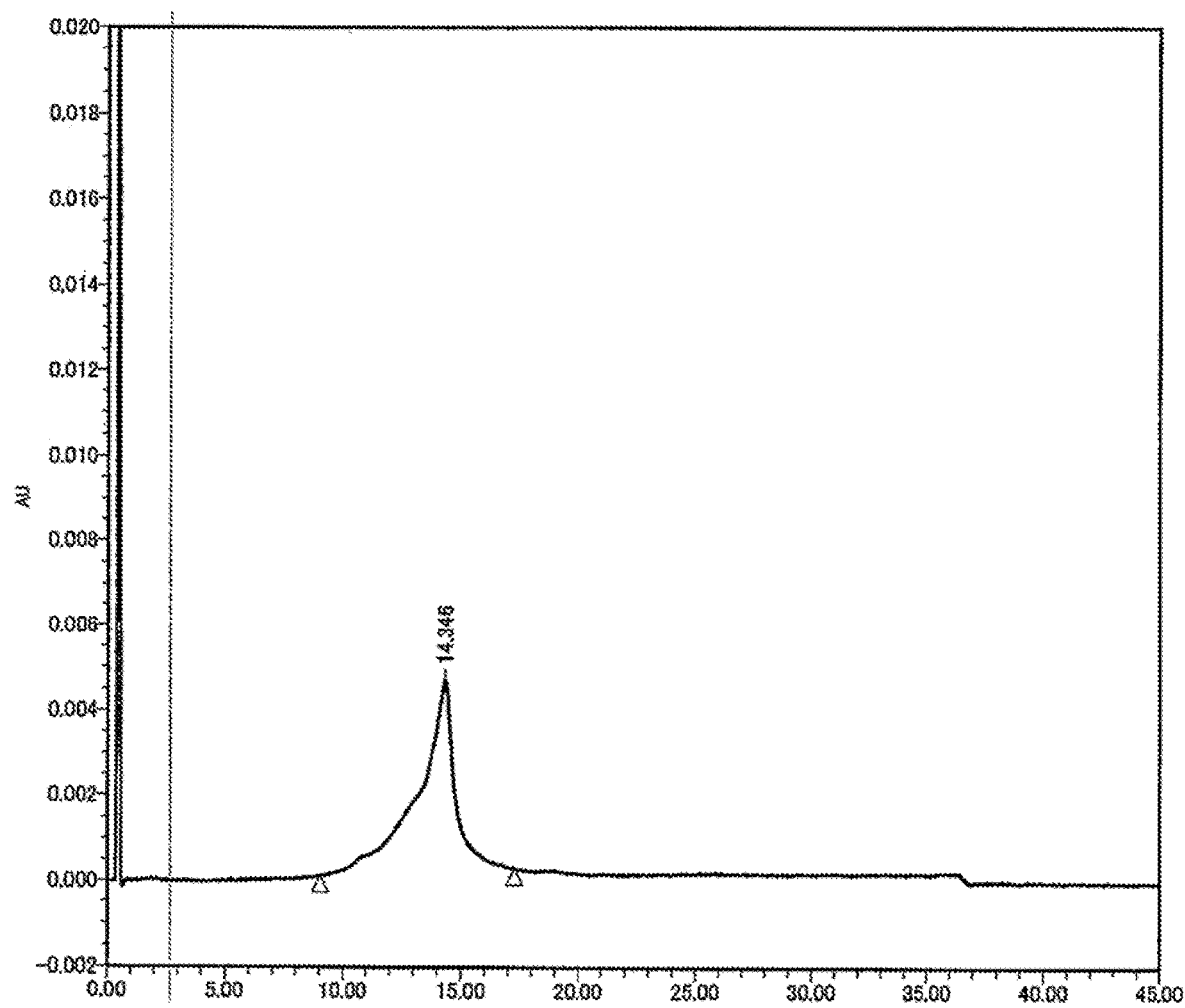
FIG. 2 is a chart of HPLC measurement using a hydrophobic interaction chromatography (HIC) column in Comparative Example 7.
Figure 3:
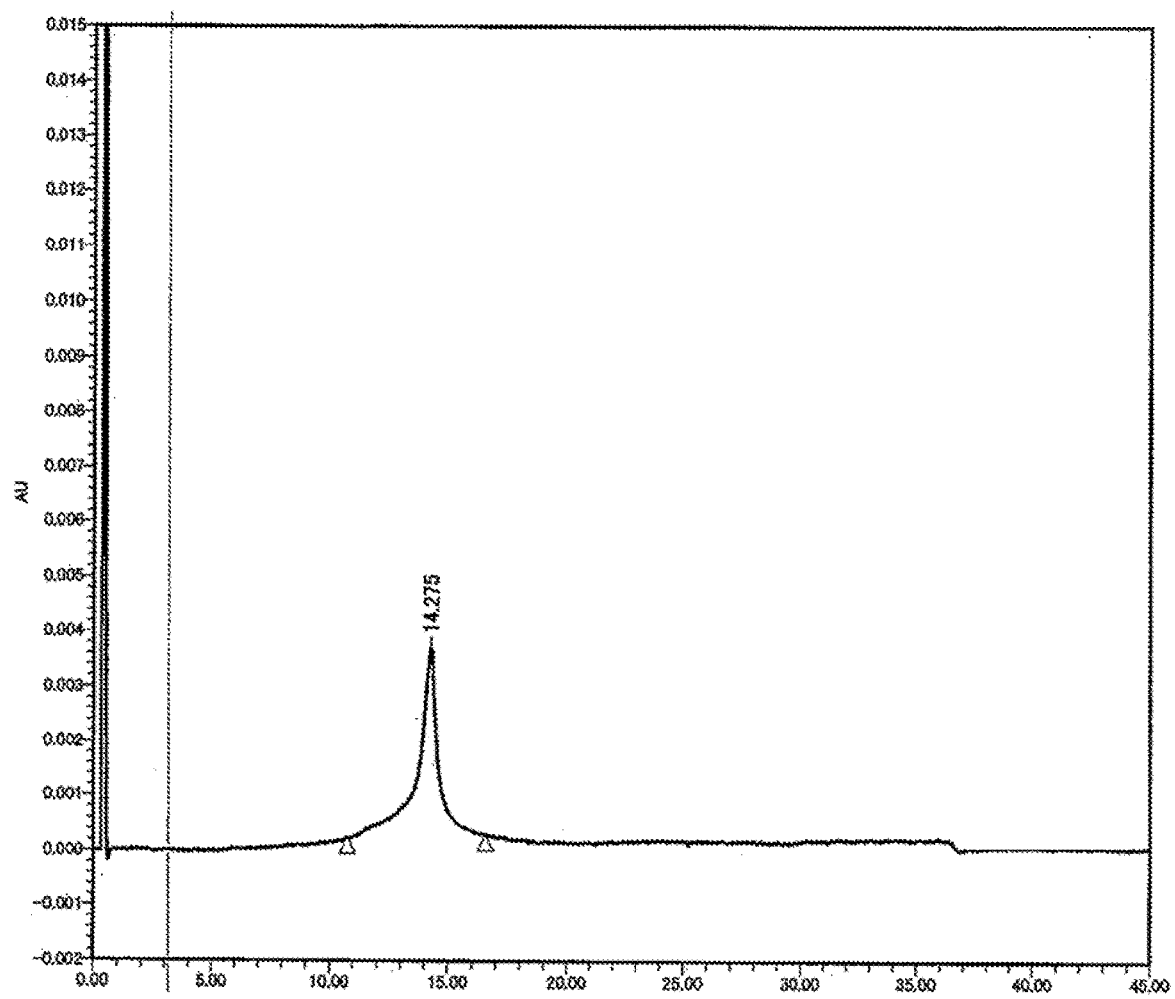
FIG. 3 is a chart of HPLC measurement using a hydrophobic interaction chromatography (HIC) column in Comparative Example 14.

The drug-linker compound of the formula (36) as Comparative Example was detected at a retention time of 14.3 minutes in the chart of FIG. 2, and the drug-linker compound of the formula (42) was detected at a retention time of 14.3 minutes in the chart of FIG. 3, and the retention time was on the same level regardless of the chain length of the monodispersed polyethylene glycol. On the other hand, the drug-linker compound of the formula (30) according to the invention was detected at a retention time of 11.7 minutes in the chart of FIG. 1. Therefore, it is shown that since the drug-linker compound of the formula (30) having a short retention time is less hydrophobic, the heterobifunctional monodispersed polyethylene glycol of the invention can effectively mask the hydrophobicity of a drug.

INDUSTRIAL APPLICABILITY

Since the heterobifunctional monodispersed polyethylene glycol of the present invention does not have a chiral center, a problem of the not-desired partial steric inversion or racemization of the chiral center does not fundamentally occur in the chemical conversion process and since two monodispersed polyethylene glycol side chains are bonded to a quaternary carbon atom of the branched portion by a stable ether bond, it is difficult to be decomposed into a single-chain monodispersed polyethylene glycol in the chemical conversion process. Therefore, an antibody-drug conjugate having high homogeneity can be obtained by bonding an antibody and a drug using the heterobifunctional monodispersed polyethylene glycol.

While the present invention has been described in detail and with reference to specific embodiments thereof, it will be apparent to those skilled in the art that various changes and modifications can be made therein without departing from the spirit and scope of the invention.

The present application is based on a Japanese patent application filed on Mar. 13, 2018 (Japanese Patent Application No. 2018-44992), and the contents thereof are incorporated herein by reference.

The invention claimed is:

1. A heterobifunctional monodispersed polyethylene glycol represented by the formula (1):

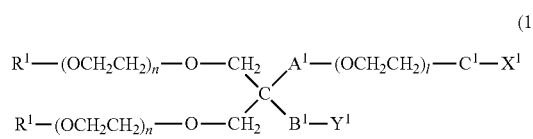

(1)

wherein, in the formula (1),
$X^1$ and $Y^1$ are each an atomic group containing at least a functional group capable of forming a covalent bond upon a reaction with a functional group present in a biofunctional molecule, the functional group contained in the atomic group $X^1$ and the functional group contained in the atomic group $Y^1$ are different from each other;
$R^1$ is a hydrocarbon group having from 1 to 7 carbon atoms or a hydrogen atom;
n is an integer of 3 to 72;
l is an integer of 2 to 72;
$A^1$ represents -$L^1$-$(CH_2)_{m1}$— or -$L^1$-$(CH_2)_{m1}$-$L^2$-$(CH_2)_{m2}$—, $L^1$ represents an ether bond, an amide bond, an urethane bond, a secondary amino group or a single bond, $L^2$ represents an amide bond or an urethane bond, and m1 and m2 represent each independently an integer of 1 to 5;
$B^1$ represents -$L^3$-$(CH_2)_{m3}$—, -$L^3$-$(CH_2)_{m3}$-$L^4$-$(CH_2)_{m4}$— or a single bond, $L^3$ represents an amide bond or a single bond, $L^4$ represents an ether bond, an amide bond or an urethane bond, and m3 and m4 represent each independently an integer of 1 to 5; and
$C^1$ represents -$L^5$-$(CH_2)_{m5}$—, —O—$CH_2$— or a single bond, $L^5$ represents an amide bond, an urethane bond, a secondary amino group or a single bond, and m5 represents an integer of 1 to 5,
wherein the functional group contained in the atomic group $X^1$ and the functional group contained in the atomic group $Y^1$ are each independently selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a 2-pyridyldithio group, an α-haloacetyl group, a hydroxy group, an alkynyl group, an allyl group, a vinyl group, an amino group, an oxyamino group, a hydrazide group, an azide group and a dibenzocyclooctyne (DBCO) group.

2. The heterobifunctional monodispersed polyethylene glycol according to claim 1, wherein, in the formula (1), $A^1$ is represented by —NHC(O)—$(CH_2)_{m1}$— or —NHC(O)—$(CH_2)_{m1}$-$L^2$-$(CH_2)_{m2}$—, $B^1$ is represented by —$(CH_2)_{m3}$— or —$(CH_2)_{m3}$-$L^4$-$(CH_2)_{m4}$—, and $C^1$ is represented by -$L^5$-$(CH_2)_{m5}$—, —O—$CH_2$— or a single bond.

3. The heterobifunctional monodispersed polyethylene glycol according to claim 1, wherein, in the formula (1), $A^1$ is represented by —$CH_2$— or —$CH_2$-$L^2$-$(CH_2)_{m2}$—, $B^1$ is represented by —$CH_2$— or —$CH_2$-$L^4$-$(CH_2)_{m4}$—, and $C^1$ is represented by -$L^5$-$(CH_2)_{m5}$—, —O—$CH_2$— or a single bond.

4. The heterobifunctional monodispersed polyethylene glycol according to claim 1, wherein, in the formula (1), $A^1$ is represented by —O—$(CH_2)_{m1}$— or —O—$(CH_2)_{m1}$-$L^2$-$(CH_2)_{m2}$—, $B^1$ is represented by —$CH_2$— or —$CH_2$-$L^4$-$(CH_2)_{m4}$—, and $C^1$ is represented by -$L^5$-$(CH_2)_{m5}$—, —O—$CH_2$— or a single bond.

5. The heterobifunctional monodispersed polyethylene glycol according to claim 1, wherein, in the formula (1), $A^1$ is represented by —C(O)NH—$(CH_2)_{m1}$— or —C(O)NH—$(CH_2)_{m1}$-$L^2$-$(CH_2)_{m2}$—, $B^1$ is represented by —$CH_2$— or —$CH_2$-$L^4$-$(CH_2)_{m4}$—, and $C^1$ is represented by -$L^5$-$(CH_2)_{m5}$—, —O—$CH_2$— or a single bond.

6. The heterobifunctional monodispersed polyethylene glycol according to claim 1, wherein, in the formula (1), $A^1$ is represented by —C(O)NH—$(CH_2)_{m1}$— or —C(O)NH—$(CH_2)_{m1}$-$L^2$-$(CH_2)_{m2}$—, $B^1$ is represented by —C(O)NH—$(CH_2)_{m3}$— or —C(O)NH—$(CH_2)_{m3}$-$L^4$-$(CH_2)_{m4}$—, and $C^1$ is represented by -$L^5$-$(CH_2)_{m5}$—, —O—$CH_2$— or a single bond.

7. The heterobifunctional monodispersed polyethylene glycol according to claim 1, wherein $X^1$ and $Y^1$ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (l), the formula (m), the formula (n) and the formula (o):

(a)

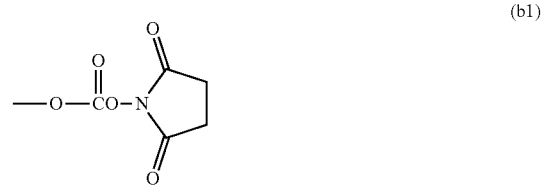

(b1)

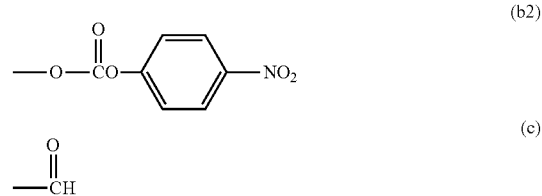

(b2)

(c)

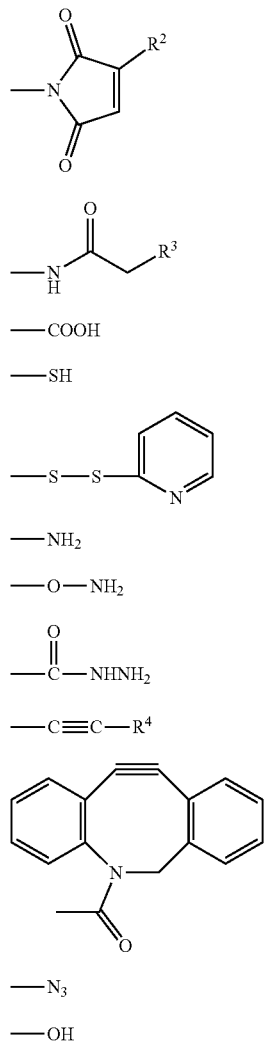
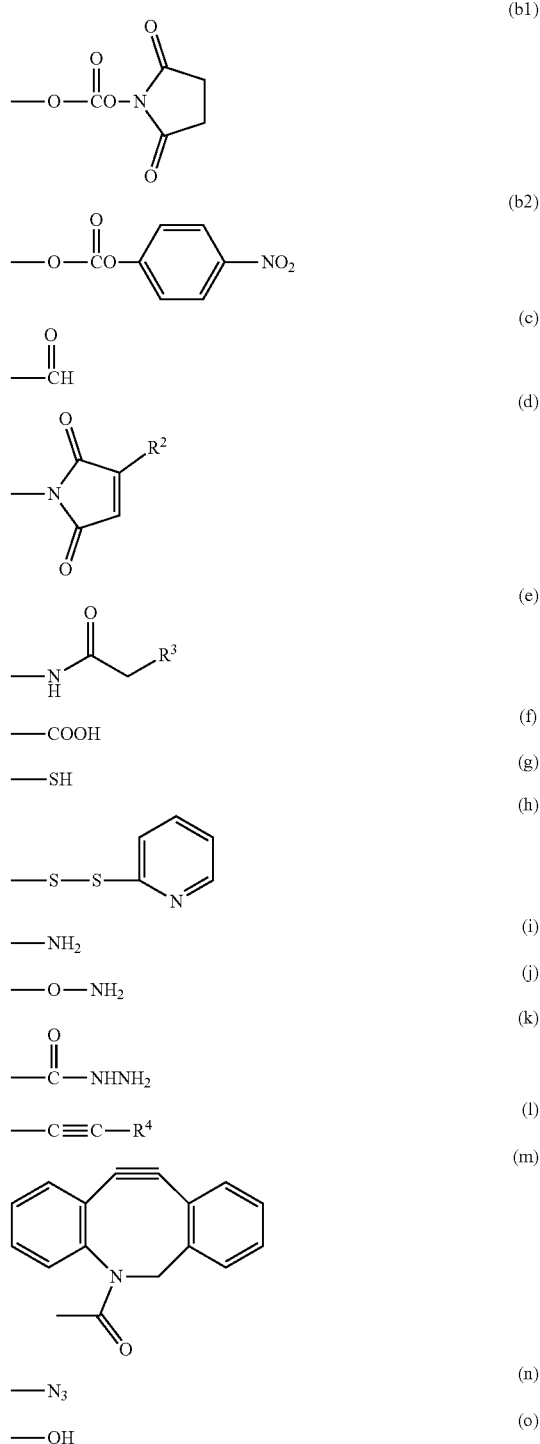

wherein, in the formula (d), $R^2$ is a hydrogen atom or a hydrocarbon group having from 1 to 5 carbon atoms; in the formula (e), $R^3$ is a halogen atom selected from a chlorine atom, a bromine atom and an iodine atom; and in the formula (1), $R^4$ is a hydrogen atom or a hydrocarbon group having from 1 to 5 carbon atoms.

8. The heterobifunctional monodispersed polyethylene glycol according to claim 2, wherein $X^1$ and $Y^1$ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (l), the formula (m), the formula (n) and the formula (o):

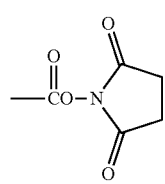

wherein, in the formula (d), $R^2$ is a hydrogen atom or a hydrocarbon group having from 1 to 5 carbon atoms; in the formula (e), $R^3$ is a halogen atom selected from a chlorine atom, a bromine atom and an iodine atom; and in the formula (1), $R^4$ is a hydrogen atom or a hydrocarbon group having from 1 to 5 carbon atoms.

9. The heterobifunctional monodispersed polyethylene glycol according to claim 3, wherein $X^1$ and $Y^1$ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (l), the formula (m), the formula (n) and the formula (o):

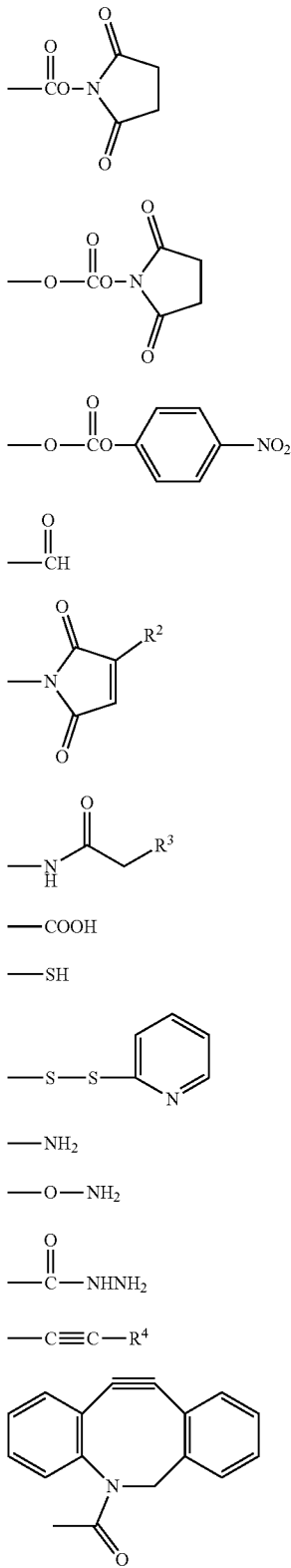

(a)
(b1)
(b2)
(c)
(d)
(e)
(f)
(g)
(h)
(i)
(j)
(k)
(l)
(m)

 (n)

—OH (o)

wherein, in the formula (d), $R^2$ is a hydrogen atom or a hydrocarbon group having from 1 to 5 carbon atoms; in the formula (e), $R^3$ is a halogen atom selected from a chlorine atom, a bromine atom and an iodine atom; and in the formula (1), $R^4$ is a hydrogen atom or a hydrocarbon group having from 1 to 5 carbon atoms.

10. The heterobifunctional monodispersed polyethylene glycol according to claim 4, wherein $X^1$ and $Y^1$ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (1), the formula (m), the formula (n) and the formula (o):

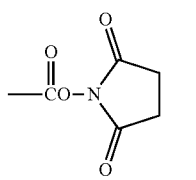 (a)

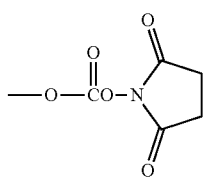 (b1)

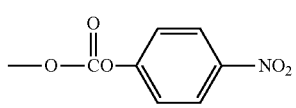 (b2)

 (c)

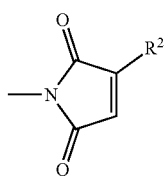 (d)

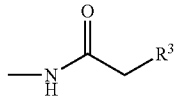 (e)

—COOH (f)

—SH (g)

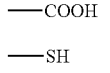 (h)

—NH$_2$ (i)

-continued

—O—NH₂ (j)

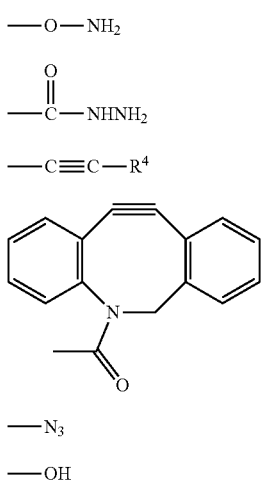

—N₃ (n)

—OH (o)

wherein, in the formula (d), R² is a hydrogen atom or a hydrocarbon group having from 1 to 5 carbon atoms; in the formula (e), R³ is a halogen atom selected from a chlorine atom, a bromine atom and an iodine atom; and in the formula (1), R⁴ is a hydrogen atom or a hydrocarbon group having from 1 to 5 carbon atoms.

11. The heterobifunctional monodispersed polyethylene glycol according to claim 5, wherein X¹ and Y¹ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (1), the formula (m), the formula (n) and the formula (o):

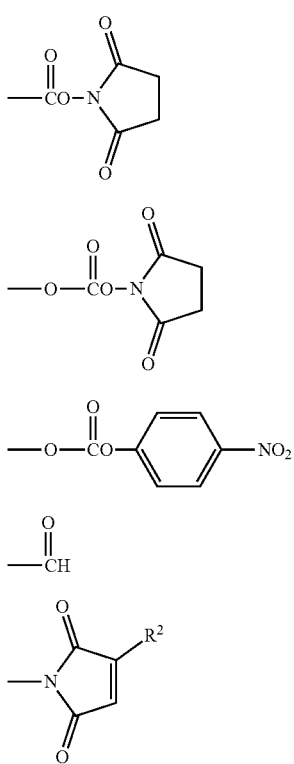

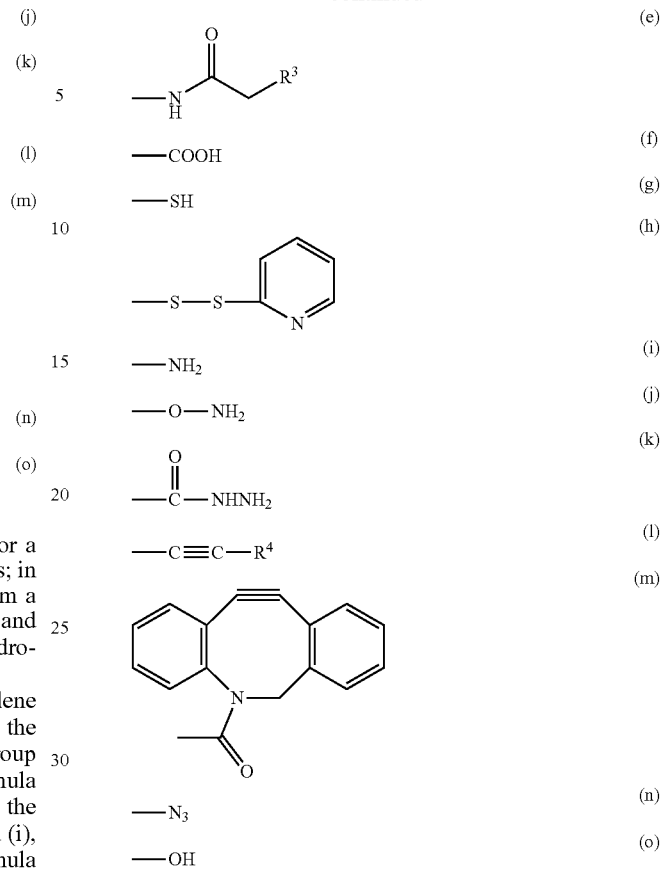

—N₃ (n)

—OH (o)

wherein, in the formula (d), R² is a hydrogen atom or a hydrocarbon group having from 1 to 5 carbon atoms; in the formula (e), R³ is a halogen atom selected from a chlorine atom, a bromine atom and an iodine atom; and in the formula (1), R⁴ is a hydrogen atom or a hydrocarbon group having from 1 to 5 carbon atoms.

12. The heterobifunctional monodispersed polyethylene glycol according to claim 6, wherein X¹ and Y¹ in the formula (1) are each independently selected from the group consisting of the formula (a), the formula (b1), the formula (b2), the formula (c), the formula (d), the formula (e), the formula (f), the formula (g), the formula (h), the formula (i), the formula (j), the formula (k), the formula (1), the formula (m), the formula (n) and the formula (o):

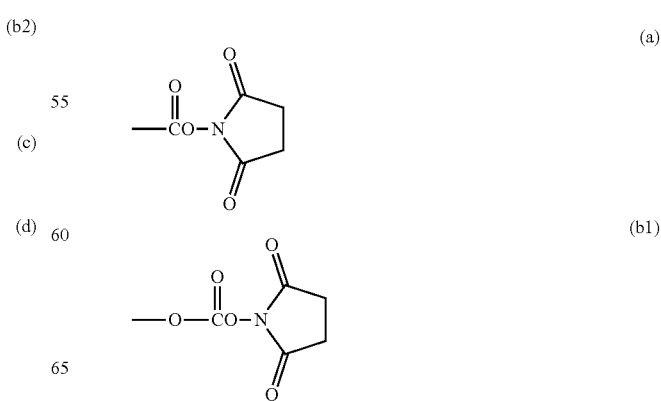

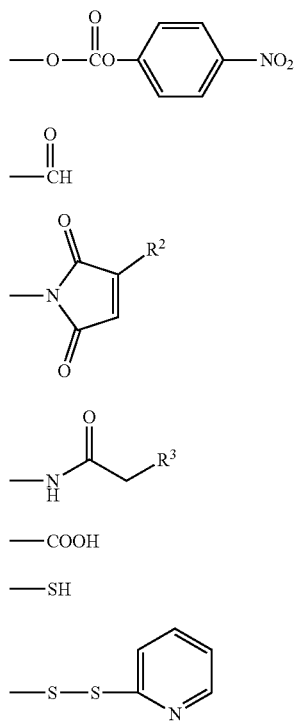
(b2)
(c)
(d)
(e)
(f) —COOH
(g) —SH
(h)
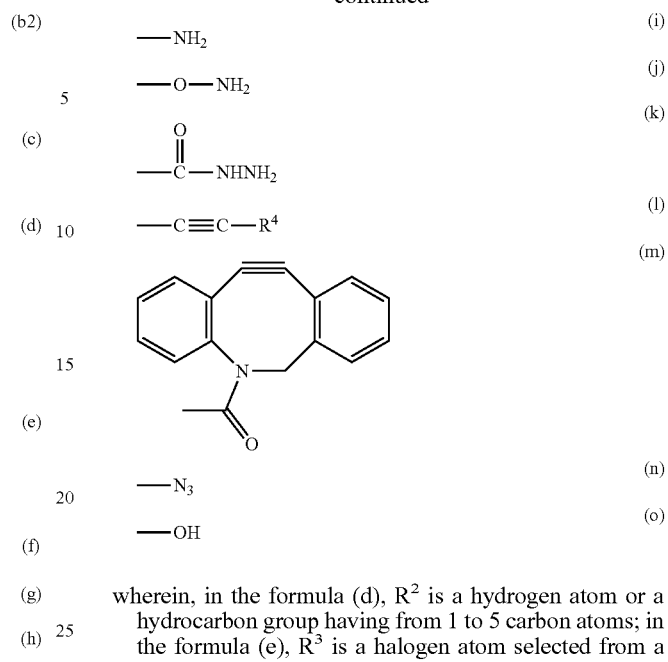
(i) —NH₂
(j) —O—NH₂
(k)
(l) —C≡C—R⁴
(m)
(n) —N₃
(o) —OH
wherein, in the formula (d), $R^2$ is a hydrogen atom or a hydrocarbon group having from 1 to 5 carbon atoms; in the formula (e), $R^3$ is a halogen atom selected from a chlorine atom, a bromine atom and an iodine atom; and in the formula (1), $R^4$ is a hydrogen atom or a hydrocarbon group having from 1 to 5 carbon atoms.
* * * * *